US008562606B2

(12) United States Patent  (10) Patent No.: US 8,562,606 B2
Richter et al.  (45) Date of Patent: Oct. 22, 2013

(54) ANKLE FUSION DEVICE, INSTRUMENTATION AND METHODS

(75) Inventors: Martinus Richter, Coburg (DE);
Michael Pinzur, Maywood, IL (US);
James DeOrio, Durham, NC (US);
Oliver Frick, Donaueschingen (DE);
Christophe Geisert, Donaueschingen (DE); Thomas Loring, Englewood, NJ (US); Stephen Gilbert, West Chester, PA (US); Victor Chan, Landing, NJ (US)

(73) Assignee: Small Bone Innovations, Inc., New York, NY (US)

( * ) Notice: Subject to any disclaimer, the term of this patent is extended or adjusted under 35 U.S.C. 154(b) by 147 days.

(21) Appl. No.: 12/965,691

(22) Filed: Dec. 10, 2010

(65) Prior Publication Data

US 2011/0282397 A1  Nov. 17, 2011

Related U.S. Application Data

(60) Provisional application No. 61/284,141, filed on Dec. 11, 2009.

(51) Int. Cl.
*A61B 17/56*  (2006.01)
(52) U.S. Cl.
USPC ............................. 606/64; 606/62
(58) Field of Classification Search
USPC ....................................... 606/62, 64
See application file for complete search history.

(56) References Cited

U.S. PATENT DOCUMENTS

| | | | |
|---|---|---|---|
| 1,863,188 | A | 8/1929 | Clash |
| 2,079,567 | A | 8/1932 | Anderson |
| 2,020,252 | A | 6/1934 | Utterbeck et al. |
| 2,101,889 | A | 12/1934 | Anderson |
| 2,185,322 | A | 3/1935 | Anderson |

(Continued)

FOREIGN PATENT DOCUMENTS

| | | |
|---|---|---|
| EP | 2047808 | 4/2009 |
| WO | 2004014243 | 2/2004 |
| WO | 2006099270 | 9/2006 |
| WO | 2010122034 | 10/2010 |

OTHER PUBLICATIONS

International Search Report and Written Opinion for PCT Application No. PCT/US2010/059937 dated May 17, 2011.
T2 Ankle Arthrodesis Nail; Ankle Arthrodesis Nailing System; Operative Technique Manual; Stryker; 2009.

(Continued)

*Primary Examiner* — Nicholas Woodall
(74) *Attorney, Agent, or Firm* — Morgan, Lewis & Bockius LLP

(57) ABSTRACT

An ankle fusion device has a proximal portion generally aligned with a first longitudinal axis. The proximal portion includes a proximal end and a first fastener hole. The proximal portion has an arcuate curve such that the proximal end is spaced a distance from the first longitudinal axis in a first direction. The first fastener hole is configured to receive a first fastener along a first fastener axis. A distal portion of the ankle fusion device extends to a distal end from the proximal portion along a second longitudinal axis. The second longitudinal axis is angled in second and third directions relative to the first longitudinal axis. The second direction is perpendicular to the first direction and the third direction being opposite the first direction. The distal portion includes a second fastener hole configured to receive a second fastener along a second fastener axis.

19 Claims, 20 Drawing Sheets

(56) References Cited

U.S. PATENT DOCUMENTS

| | | | |
|---|---|---|---|
| 2,035,952 A | 5/1935 | Ettinger | |
| 2,204,266 A | 2/1937 | Wilcox | |
| 2,393,831 A | 12/1942 | Stader | |
| 2,406,987 A | 9/1946 | Anderson | |
| 3,433,220 A * | 3/1969 | Zickel | 606/67 |
| 4,135,507 A * | 1/1979 | Harris | 606/62 |
| 4,159,716 A | 7/1979 | Borchers | |
| 4,281,649 A | 8/1981 | Derweduwen | |
| 4,308,863 A | 1/1982 | Fischer | |
| 4,338,927 A | 7/1982 | Volkov et al. | |
| 4,365,624 A | 12/1982 | Jaquet | |
| 4,622,959 A | 11/1986 | Marcus | |
| 4,733,654 A | 3/1988 | Marino | |
| 4,805,607 A | 2/1989 | Engelhardt et al. | |
| 4,827,917 A | 5/1989 | Brumfield | |
| 4,858,602 A | 8/1989 | Seidel et al. | |
| 4,875,474 A | 10/1989 | Border | |
| 4,875,475 A | 10/1989 | Comte et al. | |
| 4,877,019 A | 10/1989 | Vives | |
| 4,881,535 A | 11/1989 | Sohngen | |
| 4,889,111 A | 12/1989 | Ben-Dov | |
| 4,913,137 A | 4/1990 | Azer et al. | |
| 4,946,459 A | 8/1990 | Bradshaw et al. | |
| 5,032,125 A | 7/1991 | Durham et al. | |
| 5,034,013 A | 7/1991 | Kyle et al. | |
| 5,035,697 A | 7/1991 | Frigg | |
| 5,041,114 A | 8/1991 | Chapman et al. | |
| 5,041,115 A | 8/1991 | Frigg et al. | |
| 5,047,034 A | 9/1991 | Sohngen | |
| 5,053,035 A | 10/1991 | McLaren | |
| 5,057,110 A | 10/1991 | Kranz et al. | |
| 5,063,918 A | 11/1991 | Guhl | |
| 5,066,296 A | 11/1991 | Chapman et al. | |
| 5,078,719 A | 1/1992 | Schreiber | |
| 5,100,404 A | 3/1992 | Hayes | |
| 5,122,141 A | 6/1992 | Simpson et al. | |
| 5,167,663 A | 12/1992 | Brumfield | |
| 5,176,681 A | 1/1993 | Lawes et al. | |
| 5,178,621 A | 1/1993 | Cook et al. | |
| 5,179,915 A | 1/1993 | Cohen et al. | |
| 5,201,735 A | 4/1993 | Chapman et al. | |
| 5,263,955 A | 11/1993 | Baumgart et al. | |
| 5,268,000 A | 12/1993 | Ottieri et al. | |
| 5,312,406 A | 5/1994 | Brumfield | |
| 5,334,192 A | 8/1994 | Behrens | |
| 5,352,227 A | 10/1994 | O'Hara | |
| 5,352,228 A | 10/1994 | Kummer et al. | |
| 5,374,235 A | 12/1994 | Ahrens | |
| 5,454,813 A | 10/1995 | Lawes | |
| 5,458,600 A | 10/1995 | Stapert et al. | |
| 5,472,444 A | 12/1995 | Huebner et al. | |
| 5,480,402 A | 1/1996 | Kim | |
| 5,505,733 A | 4/1996 | Justin et al. | |
| 5,505,734 A | 4/1996 | Caniggia et al. | |
| 5,509,919 A | 4/1996 | Young | |
| 5,516,335 A | 5/1996 | Kummer et al. | |
| 5,531,748 A | 7/1996 | de la Caffiniere | |
| 5,549,610 A | 8/1996 | Russell et al. | |
| 5,562,665 A | 10/1996 | Young | |
| 5,562,666 A | 10/1996 | Brumfield | |
| 5,562,667 A | 10/1996 | Shuler et al. | |
| 5,569,249 A | 10/1996 | James et al. | |
| 5,573,536 A | 11/1996 | Grosse et al. | |
| 5,603,715 A | 2/1997 | Kessler | |
| 5,620,445 A | 4/1997 | Brosnahan et al. | |
| 5,626,580 A | 5/1997 | Brosnahan | |
| 5,628,750 A | 5/1997 | Whitlock et al. | |
| 5,653,709 A | 8/1997 | Frigg | |
| 5,658,287 A | 8/1997 | Hofmann et al. | |
| 5,658,288 A | 8/1997 | Kim | |
| 5,688,271 A | 11/1997 | Faccioli et al. | |
| 5,697,930 A * | 12/1997 | Itoman et al. | 606/62 |
| 5,713,902 A * | 2/1998 | Friedl | 606/64 |
| 5,743,908 A | 4/1998 | Kim | |
| 5,766,174 A | 6/1998 | Perry | |
| 5,779,704 A | 7/1998 | Kim | |
| 5,855,579 A | 1/1999 | James et al. | |
| 5,931,837 A | 8/1999 | Marsh et al. | |
| 5,935,127 A | 8/1999 | Border | |
| 6,010,505 A | 1/2000 | Asche et al. | |
| 6,010,506 A | 1/2000 | Gosney et al. | |
| 6,053,918 A | 4/2000 | Spievack | |
| 6,106,528 A | 8/2000 | Durham et al. | |
| 6,120,504 A | 9/2000 | Brumback et al. | |
| 6,123,708 A | 9/2000 | Kilpela et al. | |
| 6,126,661 A | 10/2000 | Faccioli et al. | |
| 6,168,595 B1 | 1/2001 | Durham et al. | |
| 6,197,029 B1 | 3/2001 | Fujimori et al. | |
| 6,221,074 B1 | 4/2001 | Cole et al. | |
| 6,228,086 B1 | 5/2001 | Wahl et al. | |
| 6,235,031 B1 | 5/2001 | Hodgeman et al. | |
| 6,270,499 B1 * | 8/2001 | Leu et al. | 606/64 |
| 6,322,591 B1 | 11/2001 | Ahrens | |
| 6,328,737 B1 | 12/2001 | Moorcroft et al. | |
| 6,383,185 B1 | 5/2002 | Baumgart | |
| 6,387,098 B1 | 5/2002 | Cole et al. | |
| 6,402,753 B1 | 6/2002 | Cole et al. | |
| 6,406,477 B1 | 6/2002 | Fujiwara | |
| 6,461,358 B1 | 10/2002 | Faccioli et al. | |
| 6,461,360 B1 * | 10/2002 | Adam | 606/67 |
| 6,508,820 B2 | 1/2003 | Bales | |
| 6,524,313 B1 | 2/2003 | Fassier et al. | |
| 6,569,165 B2 | 5/2003 | Wahl et al. | |
| 6,572,620 B1 | 6/2003 | Schon et al. | |
| 6,579,293 B1 | 6/2003 | Chandran | |
| 6,579,294 B2 | 6/2003 | Robioneck | |
| 6,652,524 B1 | 11/2003 | Weiner | |
| 6,652,528 B2 | 11/2003 | Vandewalle | |
| 6,652,529 B2 | 11/2003 | Swanson | |
| 6,746,448 B2 | 6/2004 | Weiner et al. | |
| 6,808,527 B2 | 10/2004 | Lower et al. | |
| 6,926,719 B2 | 8/2005 | Sohngen et al. | |
| 6,932,819 B2 | 8/2005 | Wahl et al. | |
| 6,964,663 B2 | 11/2005 | Grant et al. | |
| 7,001,386 B2 | 2/2006 | Sohngen et al. | |
| 7,018,380 B2 | 3/2006 | Cole | |
| 7,041,104 B1 | 5/2006 | Cole et al. | |
| 7,141,052 B2 | 11/2006 | Manderson | |
| 7,144,399 B2 | 12/2006 | Hayes et al. | |
| 7,175,633 B2 | 2/2007 | Roth et al. | |
| 7,182,765 B2 | 2/2007 | Roth et al. | |
| 7,232,442 B2 | 6/2007 | Sohngen et al. | |
| 7,232,443 B2 | 6/2007 | Zander et al. | |
| 7,341,588 B2 | 3/2008 | Swanson | |
| 7,410,488 B2 | 8/2008 | Janna et al. | |
| 7,422,593 B2 | 9/2008 | Cresina et al. | |
| 7,465,303 B2 | 12/2008 | Riccione et al. | |
| 7,479,142 B2 | 1/2009 | Weiner et al. | |
| 7,588,577 B2 | 9/2009 | Fencl et al. | |
| 7,608,074 B2 | 10/2009 | Austin et al. | |
| 7,625,409 B2 | 12/2009 | Saltzman et al. | |
| 7,749,224 B2 | 7/2010 | Cresina et al. | |
| 7,815,586 B2 | 10/2010 | Grant et al. | |
| 7,887,495 B2 | 2/2011 | Boyd et al. | |
| 7,887,498 B2 | 2/2011 | Marin | |
| 7,955,333 B2 | 6/2011 | Yeager | |
| 2004/0039394 A1 | 2/2004 | Conti et al. | |
| 2004/0133200 A1 | 7/2004 | Ruch et al. | |
| 2005/0107791 A1 | 5/2005 | Manderson | |
| 2005/0203587 A1 * | 9/2005 | Sohngen | 606/60 |
| 2006/0095039 A1 | 5/2006 | Mutchler | |
| 2006/0155276 A1 | 7/2006 | Walulik et al. | |
| 2006/0200141 A1 | 9/2006 | Janna et al. | |
| 2006/0206044 A1 | 9/2006 | Simon | |
| 2006/0235394 A1 | 10/2006 | Martin | |
| 2007/0100338 A1 | 5/2007 | Deffenbaugh et al. | |
| 2007/0123856 A1 | 5/2007 | Deffenbaugh et al. | |
| 2007/0123857 A1 | 5/2007 | Deffenbaugh et al. | |
| 2007/0276385 A1 | 11/2007 | Schlienger et al. | |
| 2008/0015587 A1 | 1/2008 | Munoz | |
| 2008/0294164 A1 | 11/2008 | Frank et al. | |
| 2009/0099571 A1 | 4/2009 | Cresina et al. | |
| 2009/0149861 A1 | 6/2009 | Brodsky et al. | |

(56) References Cited

U.S. PATENT DOCUMENTS

2009/0275944 A1 11/2009 Huebner et al.
2011/0082458 A1 4/2011 Crozet et al.
2011/0166608 A1 7/2011 Duggal et al.

OTHER PUBLICATIONS

The Titanium Cannulated Hindfoot Arthrodesis Nail, Expert Nailing System: Technique Guide; Synthes; 2007.

* cited by examiner

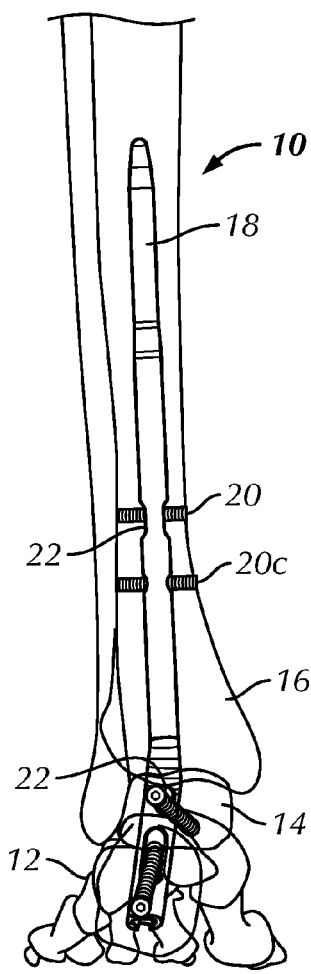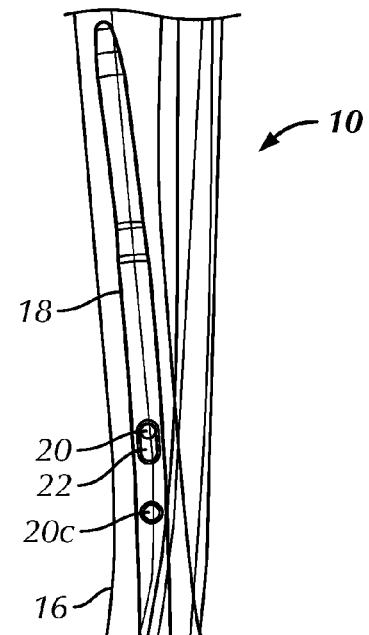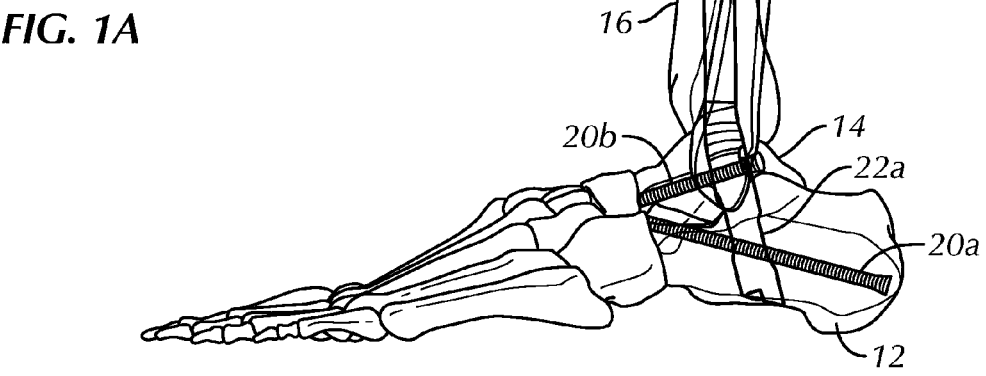
FIG. 1A
FIG. 1B

ANKLE FUSION DEVICE, INSTRUMENTATION AND METHODS

CROSS-REFERENCE TO RELATED APPLICATIONS

This application claims the benefit of U.S. Provisional Patent Application No. 61/284,141 filed Dec. 11, 2009 and entitled "Ankle Fusion Device and Method" which is hereby incorporated by reference in its entirety.

BACKGROUND OF THE INVENTION

The present invention, according to some embodiments, includes an implantable device, instrumentation and methods for fusing ankle bones of a mammalian patient. More particularly, in some embodiments, the invention is directed to an arthrodesis nail and instrumentation and methods for implanting the same to fuse the tibia, talus, and calcaneus bones of an ankle of a human patient.

BRIEF SUMMARY OF THE INVENTION

In one embodiment there is an ankle fusion device that includes a proximal portion generally extending along a first longitudinal axis. The proximal portion includes a proximal end and a first fastener hole. The proximal portion has an arcuate curve such that the proximal end is spaced a distance from the first longitudinal axis in a first direction. The first fastener hole is configured to receive a first fastener along a first fastener axis. A distal portion of the ankle fusion device extends to a distal end from the proximal portion along a second longitudinal axis. The second longitudinal axis is angled in second and third directions relative to the first longitudinal axis. The second direction is perpendicular to the first direction and the third direction is opposite the first direction. The distal portion includes a second fastener hole configured to receive a second fastener along a second fastener axis. In one embodiment, the second fastener hole is elongate and the distal portion further includes a bore extending proximally from the distal end along the second longitudinal axis. The bore is at least partially threaded. The distal portion further includes an elongate third fastener hole configured to receive a third fastener along a third fastener axis.

In a further embodiment, the ankle fusion device comprises a compression screw configured to be received in the bore and translate therein along the second longitudinal axis. In on embodiment, the compression screw includes an engagement portion having a concave surface configured to contact the third fastener when the third fastener is received in the third fastener hole and a threaded portion attachable to the engagement portion and having external threads configured to engage the threads of the bore. In one embodiment, the bore does not extend through the entire distal portion.

In a further embodiment, the ankle fusion device further comprises an end cap set screw having a closed distal end and external screws configured to engage the threads of the bore. In one embodiment, the distal portion includes a third fastener hole configured to receive a third fastener along a third fastener axis. In one embodiment, the second fastener axis is oriented at an oblique angle relative to the third fastener axis. In one embodiment, the second fastener axis and the third fastener axis lie on planes that are parallel to one another. In one embodiment, the third fastener axis is configured to be substantially aligned with a longest dimension of a talus once the ankle fusion device is implanted. In one embodiment, the proximal portion further comprises a fourth fastener hole configured to receive a fourth fastener along a fourth fastener axis. In one embodiment, the fourth fastener axis and the first fastener axis are substantially parallel. In one embodiment, the fourth fastener hole is elongate.

In one embodiment, the distal end includes a truncated surface that is generally perpendicular to the first longitudinal axis and oriented at an oblique angle relative to the second longitudinal axis. In one embodiment, the second fastener axis is configured to be substantially aligned with a longest dimension of a calcaneus bone once the ankle fusion device is implanted. In one embodiment, once the ankle fusion device is implanted in a body the proximal portion extends into a tibia, the distal portion extends through a calcaneus, the first direction is in an anterior direction, the second direction is in a lateral direction and the third direction is in a posterior direction. In one embodiment, the entire proximal portion is arcuate in the first direction. In one embodiment, the proximal portion is least partially cannulated. In one embodiment, the proximal portion is substantially solid.

In another embodiment, a device for positioning at least one guidewire in a calcaneus bone and talus bone comprises a frame configured and dimensioned to at least partially surround the calcaneus bone and the talus bone. The frame includes a guidewire target configured and dimensioned to be inserted between the talus bone and a tibia bone proximate a talar dome of the talus bone and a first guidewire sleeve radially disposed about a first guidewire axis. The first guidewire axis is aligned with the guidewire target.

In a further embodiment, the device includes a second guidewire template attached to the frame and having a second guidewire sleeve radially disposed about a second guidewire axis. In one embodiment, the second guidewire template includes an alignment guide extending therefrom. In one embodiment, the second guidewire axis extends towards the guidewire target when the alignment guide is substantially aligned with a pre-selected anatomical feature. In one embodiment, the pre-selected anatomical feature is a second metatarsal bone. In one embodiment, the second guidewire axis is positioned at an oblique angle relative to the first guidewire axis when the alignment guide is substantially aligned with the pre-selected anatomical feature. In on embodiment, the second guidewire template is configured to rotate about the first guidewire axis. In one embodiment, the second guidewire template is slideable and rotatable relative to the first guidewire sleeve.

In a further embodiment, the device includes a tibial alignment guide engaged with the frame and configured to extend proximally therefrom along a longitudinal axis substantially parallel to the first guidewire axis. In one embodiment, the tibial alignment guide includes a transverse member being positionable at a location along a longitudinal axis of the tibial alignment guide. In one embodiment, the transverse member has a curvature about the first guidewire axis. In one embodiment, the frame further comprises a targeting arm that includes the guidewire target and the tibial member is attachable to the targeting arm. In one embodiment, an extension of the tibial alignment guide includes at least one alignment member, the at least one alignment member configured and positioned to intersect with a plane aligned with the first guidewire axis. In one embodiment, the tibial alignment guide is rotatably attachable with the frame.

In one embodiment, the frame further comprises a targeting arm that includes the guidewire target, the targeting arm and the first sleeve arm being substantially parallel to one another. In one embodiment, the first sleeve is fixed in position relative to the targeting arm. In one embodiment, the first guidewire axis is configured to substantially align with a center of the talar dome and to the guidewire target when the guidewire target is inserted between the talus and the tibia proximate the talar dome. In one embodiment, the first sleeve arm is positioned distally from the calcaneus bone when the guidewire target is inserted between the talus bone and the tibia bone proximate the talar dome of the talus bone.

In another embodiment, a method for positioning a guidewire in a calcaneus bone, talus bone, and tibia bone, includes: inserting a guidewire target on a guidewire targeting device into an ankle joint at a distal end of the tibia bone such that the guidewire target is proximate a talar dome of the talus bone; positioning a first guidewire sleeve on the guidewire targeting device proximate the calcaneus bone, the first guidewire sleeve pointing toward the guidewire target to provide a first guidewire axis; aligning the first guidewire axis of the first guidewire sleeve generally co-axially with a longitudinal axis of the tibia bone; and advancing a first guidewire along the first guidewire axis through the first guidewire sleeve and into the distal tibia bone through the calcaneus bone and talar dome of the talus bone.

In a further embodiment, the method includes: positioning a second guidewire axis of a guidewire template coupled to the guidewire targeting device at an oblique angle relative to the first guidewire axis; aligning the second guidewire axis with the talar dome of the talus bone and; and advancing a second guidewire along the second guidewire axis through a second guidewire sleeve on the guidewire temple and into the calcaneus bone and the talar bone until an end of the second guidewire generally reaches the first guidewire.

In one embodiment, the second guidewire axis includes rotating the guidewire template relative to the guidewire targeting device until an alignment arm of the guidewire template is substantially aligned with an anatomical feature. In one embodiment, the anatomical feature is a long axis of a second metatarsal bone. In one embodiment, the guidewire template is rotatably coupled to the guidewire targeting device. In one embodiment, the guidewire temple is slideably coupled over a portion of the first guidewire sleeve surrounding the first guidewire axis.

In a further embodiment, the method includes: removing the first guidewire; advancing a cannulated resection device over the second guidewire and through the calcaneus and the talus; performing a dorsiflexion and inversion of the ankle joint to align the second guidewire with the longitudinal axis of the tibia bone; advancing the second guidewire into the tibia bone along the longitudinal axis of the tibia bone; and further advancing the cannulated resection device over the second guidewire and into the tibia.

In one embodiment, the second guidewire axis is angled laterally and posteriorly relative to the first guidewire axis. In a further embodiment, the method comprises: positioning an elongate member coupled with the guidewire targeting device substantially parallel to the longitudinal axis of the tibia bone. In one embodiment, a proximal arm extends from the guidewire target and a distal arm extends from the first guidewire sleeve, the proximal arm being generally parallel to and spaced from the distal arm. In one embodiment, aligning the first guidewire axis includes aligning the guidewire target with a center of the talar dome.

In a further embodiment, the method includes bracing an alignment guide of the guidewire targeting device against an anterior surface of an outside of a leg. In one embodiment, aligning the first guidewire axis of the first guidewire sleeve generally co-axially with the longitudinal axis of the tibia bone includes positioning an alignment member of the guidewire targeting device proximal the tibia bone on a plane aligned with the longitudinal axis of the tibia bone.

BRIEF DESCRIPTION OF THE SEVERAL VIEWS OF THE DRAWINGS

The foregoing summary, as well as the following detailed description of embodiments of the Ankle Fusion Device, Instrumentation and Methods, will be better understood when read in conjunction with the appended drawings of an exemplary embodiment. It should be understood, however, that the invention is not limited to the precise arrangements and instrumentalities shown.

In the drawings:

FIG. 1A is a posterior elevational view of an ankle fusion device including a nail in accordance with an exemplary embodiment of the present invention shown implanted in a semi-transparent skeleton;

FIG. 1B is a lateral elevational view of the nail shown in FIG. 1A;

DETAILED DESCRIPTION OF THE INVENTION

Figure 2A:
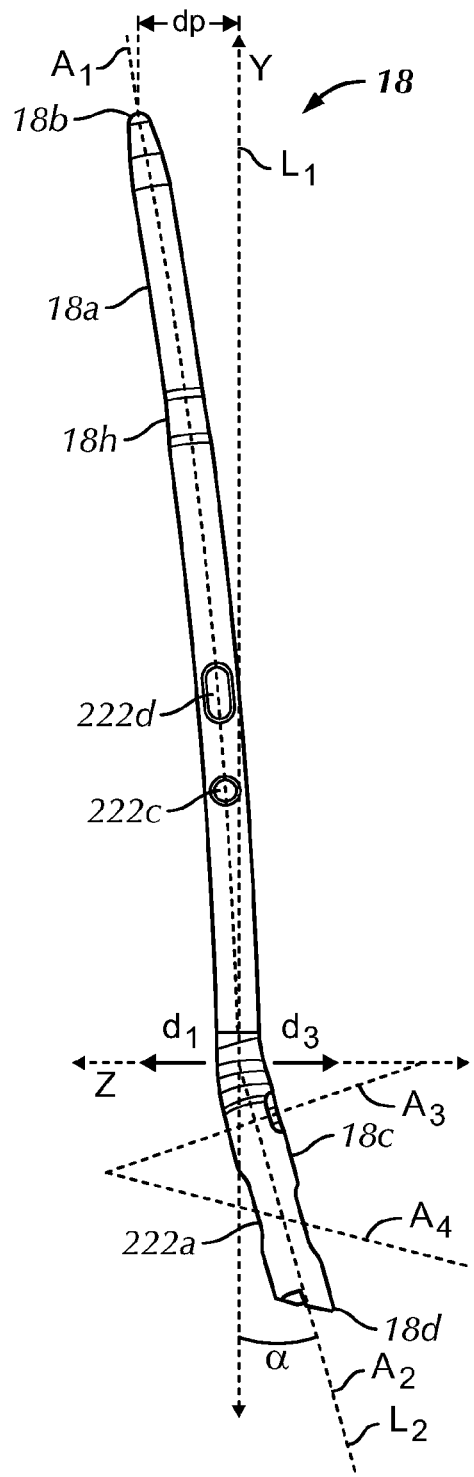
FIG. 2A is a lateral elevational view of the nail of FIG. 1A.

Referring to the drawings in detail, wherein like reference numerals indicate like elements throughout, there is shown in FIGS. 1A-24 an ankle fusion device, generally designated 10, and various instrumentation for implanting the same, in accordance with exemplary embodiments of the present invention.

Severe arthrosis and deformity of the ankle and subtalar joints may be debilitating problems that can be difficult to treat. Tibotalocalcaneal fusion (fusion of the calcaneus, talus and tibia) with an intramedullary nail can be considered a salvage procedure for severe arthrosis and deformity of the ankle and subtalar joints. Ankle arthrodesis may be a challenging procedure due to poor host conditions (e.g., bad skin, deformity, and avascular necrosis), inability to get adequate fixation for this slow healing process, and the inability to get adequate compression across the fusion. Performing an ankle arthrodesis can also be technically demanding because of the shape and small size of the talus and calcaneus. Furthermore, known methods of installing ankle arthrodeses may limit the optimal configuration of the nail and fixation screws.

Embodiments of ankle fusion device 10 are configured and shaped to obtain more optimal bony purchase in the calcaneus 12 and talus 14 and/or increase comfort. In some embodiments, ankle fusion device 10 obtains more optimal bony purchase and/or increase comfort by more accurately approximating the anatomy of the lower limb and using the instrumentation and methods described below to prepare the bones for implanting ankle fusion device 10. The embodiments disclosed below and shown in the drawings are for the left ankle. If not otherwise mentioned below, ankle fusion device 10, the instrumentation and methods are mirrored across the sagittal plane of the body for the right ankle.

Referring to FIGS. 1A and 1B, an exemplary ankle fusion device 10 is shown implanted within the calcaneus 12, talus 14 and tibia 16 of a patient. Ankle fusion device 10 includes a nail 18 and a plurality of fasteners 20. Fasteners 20 may include any fastening device such as but not limited to pegs, nails, wires, screws, fixation screws, bone screws and locking screws. In some embodiments, nail 18 is constructed from titanium, stainless steel, alloy, ceramic, and/or other solid biocompatible material. In some embodiments, nail 18 is substantially rigid. In some embodiments, at least a portion of an exterior surface of nail 18 is treated to improve biocompatibility and/or osteointegration (e.g., textured, titanium plasma spray coating, hydroxyapatite coating, etc.).

Figure 2B:
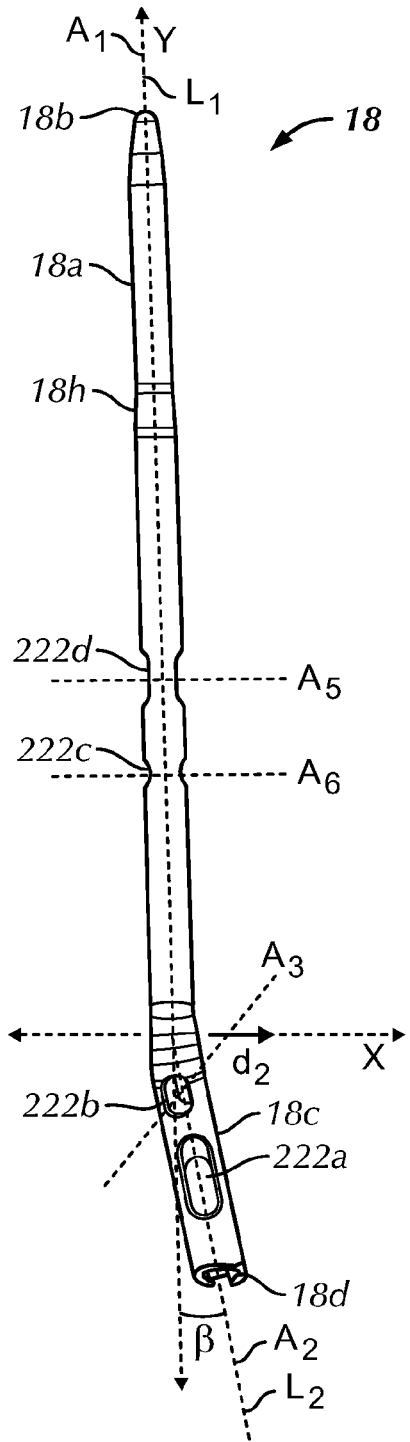
FIG. 2B is an anterior elevational view of the nail of FIG. 1A.

Referring to FIGS. 2A and 2B, an exemplary embodiment of nail 18 for the left ankle is shown. Nail 18 includes a proximal portion 18a having an axis $A_1$ generally extending along, or in the direction of, a first longitudinal axis $L_1$ that corresponds to the general vertical center of tibia 16 (or in other words, proximal portion 18a is generally perpendicular to a transverse plane of the patient). Proximal portion 18a includes a proximal end 18b and at least one fastener hole (e.g., fastener hole 222c) for receiving a fastener 20. Nail 18 also includes a distal portion 18c extending to a distal end 18d from proximal portion 18a along a second longitudinal axis $L_2$ co-axially aligned with axis $A_2$. Second longitudinal axis $L_2$ is oriented at an oblique angle relative to first longitudinal axis $L_1$. In one embodiment, nail 18 extends laterally and proximally downwardly or ventrally through the calcaneus once implanted.

In one embodiment, nail 18 also arcs anteriorly as it extends upwardly through the tibia 16 such that at least a portion of proximal portion 18a is arcuate. In one embodiment, the entire proximal portion 18a is arcuate. In one embodiment first longitudinal axis $L_1$ is tangent to the distal most end of axis $A_1$ of proximal portion 18a. Having an arcuate proximal portion 18a may help in positioning and/or fixing nail 18 within the canal of tibia 16. In one embodiment, proximal portion 18a has an arcuate curve such that proximal end 18b is spaced a distance $d_p$ from first longitudinal axis $L_1$ in a first direction $d_1$. In one embodiment, distance $d_p$ is about 36 mm for a 300 mm long nail 18. In one embodiment, proximal portion 18a has a radius of curvature of about 1.5 m. In one embodiment, the radius of curvature of proximal portion 18a is generally equal to the radius of curvature of an anterior tibial canal surface.

In one embodiment, proximal end 18b is spaced a distance $d_p$ from first longitudinal axis $L_1$ in a first direction $d_1$ and second longitudinal axis $L_2$ is oriented at oblique angles in second and third directions $d_2$, $d_3$ relative to first longitudinal axis $L_1$. In one embodiment, second direction $d_2$ is perpendicular to first direction $d_1$ and third direction $d_3$ is opposite first direction $d_1$. In one embodiment, once nail 18 is implanted, first direction $d_1$ corresponds to a forward or anterior direction, second direction $d_2$ corresponds to an outward or lateral direction and third direction $d_3$ corresponds to a rear or posterior direction relative to the ankle. In an alternative embodiment, proximal portion 18a is substantially straight. In one such embodiment, proximal portion 18a is co-axial with first longitudinal axis $L_1$.

In one embodiment, once ankle fusion device 10 is implanted in a body, proximal portion 18a extends into tibia 16, distal portion 18c extends through calcaneus 12, first direction $d_1$ is in an anterior direction, second direction $d_2$ is in a lateral direction and third direction $d_3$ is in a posterior direction. In some embodiments, proximal end 18b is tapered or pointed, in order to facilitate insertion into the canal of tibia 16. In some embodiment, proximal end 18b is tapered and configured to prevent a stress concentration on the canal of tibia 16 once nail 18 is implanted that may otherwise be caused by a nail end having a sharp edge. In one embodiment, proximal end 18b is a blunt or rounded tip. In one embodiment, proximal end 18b is closed.

In one embodiment, nail 18 has a generally circular cross section throughout its length. In alternative embodiments, nail 18 may have any cross section shape including but not limited to square, star, rectangular and triangular. In one embodiment, nail 18 has a plurality of sections that decrease in diameter toward a proximal end 18b. In some embodiments, nail 18 tapers or decreases in cross sectional size between distal portion 18c and proximal portion 18a. In some embodiments, distal portion 18c has a larger diameter than the largest diameter of proximal portion 18a. In one embodiment, distal portion 18c has a substantially constant diameter. In one embodiment, distal portion 18c has a diameter of about 8 mm to about 18 mm. In one embodiment, distal portion 18c has a diameter of about 13 mm.

In some embodiments, proximal portion 18a includes a smaller diameter section and a larger diameter section. In one embodiment, the smaller diameter section is about 7 mm to about 11 mm. In one embodiment, the smaller diameter section is about 9 mm. In one embodiment, the larger diameter section is about 10 mm. In one embodiment, the larger diameter section is about 11.5 mm. In one embodiment, the larger diameter section is about 13 mm. In some embodiments, at least a portion of the larger diameter section is hollow. In some embodiments, the smaller diameter section is not hollow. In some embodiments, the smaller diameter section is proximal to the larger diameter section and distal to proximal end 18b. In some embodiments, nail 18 is substantially solid. In some embodiments, nail 18 is hollow or cannulated.

In some embodiments, proximal portion 18a includes a frustoconical section 18h providing a transition between the larger diameter section and the smaller diameter section of the proximal portion 18a. In some embodiments, frustoconical section 18h is located at or proximate the center of the proximal portion 18a (e.g., about midway along the length of proximal portion 18a). In some embodiments, the smaller diameter section is shorter than the larger diameter section.

In other embodiments, the smaller diameter section is longer than the larger diameter section. in some embodiments, the smaller diameter section and the larger diameter section have lengths that are substantially equal. In some embodiments, nail 18 has a length of about 200 mm to about 300 mm.

In some embodiments, distal portion 18c is configured to be positioned, at least partially, in talus and calcaneus bones 14, 12 of an ankle of the patient. In some embodiments, distal portion 18c is oriented at an oblique angle relative to proximal portion 18a to maximize purchase of distal portion 18c in talus 14 and calcaneus 12 upon implantation of ankle fusion device 10. In some embodiments, distal portion 18c is configured to be positioned in talus 14 and calcaneus 12 so as to generally pass through the center of talus 14 and calcaneus 12. In some embodiments, upon implantation, distal portion 18c is angled posteriorly and/or laterally relative to proximal portion 18a. In some embodiments, upon implantation, distal portion 18c is angled posteriorly and/or laterally relative to a longitudinal axis of the tibia bone.

In the exemplary embodiment shown in FIGS. 2A and 2B, second longitudinal axis $L_2$ is oriented at an oblique angle relative to first longitudinal axis $L_1$ in third direction $d_3$ at an angle α of about 15 degrees as projected on to a coronal or x-y plane as shown in FIG. 2A. In the exemplary embodiment shown, second longitudinal axis $L_2$ is oriented at an oblique angle from first longitudinal axis $L_1$ in second direction $d_2$ at an angle β of about 10 degrees as projected on to a sagittal or y-z plane as shown in FIG. 2B. In an example for the embodiment shown, if nail 18 were removed, inverting the left foot 10 degrees and dorsiflexing the foot 15 degrees would co-axially align second longitudinal axis $L_2$ and first longitudinal axis $L_1$. In other embodiments, angle α may be about 5 degrees, about 6 degrees, about 7 degrees, about 8 degrees, about 9 degrees, about 10 degrees, about 11 degrees, about 12 degrees, about 13 degrees, about 14 degrees, exactly 15 degrees, about 16 degrees, about 17 degrees, about 18 degrees, about 19 degrees, about 20 degrees, about 21 degrees, about 22 degrees, about 23 degrees, about 24 degrees, about 25 degrees. In other embodiments, angle β may be about 1 degree, about 2 degrees, about 3 degrees, about 4 degrees, about 5 degrees, about 6 degrees, about 7 degrees, about 8 degrees, about 9 degrees, exactly 10 degrees, about 11 degrees, about 12 degrees, about 13 degrees, about 14 degrees, about 16 degrees, about 17 degrees, about 18 degrees, about 19 degrees, about 20 degrees.

Referring to FIGS. 1A and 1B, fastener holes 22 (e.g., 222a, 222b, 222c, 222d) extending through nail 18 are spaced along the length of nail 18 and are configured to receive fasteners 20. In some embodiments, ankle fusion device 10 includes a plurality of through holes or fastener holes 22, at least two of which being positioned at different locations along the length of nail 18, such that one of the at least two fastener holes 22 is positioned on nail 18 proximally or distally relative to the other fastener hole 22. In some embodiments, the ankle fusion device 10 includes a plurality of fastener holes 22, at least two of which are positioned at different radial locations about first and/or second longitudinal axes $L_1$, $L_2$ of nail 18. In some embodiments, one or more fastener holes 22 are positioned such that the central axes (see e.g., $A_3$-$A_6$) of each fastener hole 22 are substantially perpendicular to first and/or second longitudinal axis $L_1$, $L_2$ of nail 18. In some embodiments, one or more fastener holes 22 are oriented such that the central axes (e.g., $A_3$-$A_6$) through the one or more fastener holes 22 are not perpendicular to first and/or second longitudinal axis $L_1$, $L_2$ of nail 18. In some embodiments, ankle fusion device 10 includes a plurality of fastener holes 22, at least two of which are differently sized. In some embodiments, ankle fusion device 10 includes a plurality of fastener holes 22, at least two of which are substantially the same size. In some embodiments, at least some fastener holes 22 may have elongate openings, for example, elongated in a distal-proximal direction such that a fastener 20 positioned in such a fastener hole 22 is capable of shifting proximally or distally within the fastener hole 22. In some embodiments, at least some of fastener holes 22 (e.g, fastener hole 222c) may have substantially circular openings.

In one embodiment, a first fastener hole 222a is configured to receive a first fastener 20a for securing nail 18 to calcaneus 12 that is substantially co-axially aligned with a longest dimension of calcaneus 12 as shown. In one embodiment, first fastener hole 222a is aligned with a central portion of calcaneus 12. For example, first fastener hole 222a may be configured and oriented to have a central axis $A_4$ substantially co-axially aligned with a central longitudinal axis of calcaneus 12. Co-axial alignment of central axis $A_4$ with a central portion of the calcaneus bone allows first fastener 222a, in some embodiments, to find greater purchase in calcaneus 12 and to permit a stronger securement thereto. In one embodiment, the central longitudinal axis of calcaneus 12 generally extends in an anterior direction. In some embodiments, first fastener 20a has a length substantially matching the length of calcaneus 12 along a central longitudinal axis of calcaneus 12. In some embodiments, first fastener 20a is about 70 mm to about 100 mm.

In one embodiment, a second fastener hole 222b is configured to receive a second fastener 20b for securing nail 18 to talus 14 that is substantially co-axially aligned with a longest dimension of talus 14 as shown. For example, second fastener hole 222b may be configured (e.g., angled) to have a central axis $A_3$ substantially co-axially aligned with a central longitudinal axis of talus 14. In one embodiment, the central longitudinal axis of talus 14 generally extends in an anterior direction. In one embodiment, the central longitudinal axis of talus 14 generally extends in an anterior-medial direction. Co-axial alignment of the second fastener hole 222b with a central portion of the talus bone allows the second fastener 20b, in some embodiments, to find greater purchase in the talus 14 and to permit a stronger securement thereto. In one embodiment, the central longitudinal axis of talus 14 generally extends in an anterior-lateral direction. In some embodiments, second fastener 20b has a length substantially matching the length of talus 14 along a central longitudinal axis of the talus 14. In some embodiments, second fastener 20b is about 46 mm to about 80 mm.

Preferably, the central axes of the first and second elongate fastener holes 222a, 222b are divergent (e.g., as they extend anteriorly), such that the central axes are not parallel and/or not coplanar. Furthermore, the first elongate fastener hole 222a may have a different (e.g., larger) dimension than the second elongate fastener hole 222b, for example, so as to accept larger fasteners and/or permit greater shifting of the fastener.

Referring to FIGS. 2A and 2B, in one embodiment, first fastener hole 222a is elongated such that first fastener 20a can be translated proximally with respect to second longitudinal axis $L_2$ while being parallel with axis $A_4$. In one embodiment, axis $A_4$ is about 25 degrees to about 35 degrees relative to second longitudinal axis $L_2$. In one embodiment, axis $A_4$ is about 30 degrees relative to second longitudinal axis $L_2$. In one embodiment, second fastener hole 222b is elongated such that second fastener 20b can be translated with respect to second longitudinal axis $L_2$ while being parallel with axis $A_3$. In one embodiment, axis $A_3$ is about 85 degrees to about 95 degrees relative to second longitudinal axis $L_2$. In one embodiment, axis $A_3$ is generally perpendicular to second longitudinal axis $L_2$. In alternative embodiments, first and second fastener holes 222a, 222b are not elongated such that the respective fastener 20a, 20b generally cannot translate relative to nail 18.

Proximal portion 18a includes at least one fastener hole 22. In one embodiment, proximal portion 18a of nail 18 includes a locking or static fastener hole 222c. In such an embodiment, the locking fastener hole 222c is configured to receive a third fastener 20c and sized to substantially prevent translational movement of third fastener 20c relative to nail 18. In one embodiment, proximal portion 18a of nail 18 includes a dynamic fastener hole 222d. In one embodiment, dynamic fastener hole 222d is elongated such that nail 18 can be translated proximally with respect to a fourth fastener 20d extending through dynamic fastener hole 222d. In such an embodiment and as described in further detail below, fourth fastener 20d is installed toward the proximal end of dynamic fastener hole 222d such that nail 18 is substantially prevented from moving distally with respect to tibia 16 but allows for a predetermined amount of proximal movement to allow for, for example, additional compression of the ankle joint. Either one of or both third fastener 20c and fourth fastener 20d may be used depending on whether it is desired to fix nail 18 relative to tibia 16.

In one embodiment, dynamic fastener hole 222d has an axis $A_5$ such that fourth fastener 20d can be translated distally with respect to first longitudinal axis $L_1$ while being parallel with axis $A_5$. In one embodiment, axis $A_5$ is substantially perpendicular to first longitudinal axis $L_1$ in the coronal or x-y plane as shown in FIG. 2B. In one embodiment, locking fastener hole 222c has an axis $A_6$ that is substantially aligned with third fastener 20c. In one embodiment, axis $A_6$ is substantially perpendicular to first longitudinal axis $L_1$ in the coronal or x-y plane as shown in FIG. 2B. In one embodiment, axes $A_5$ and $A_6$ are substantially parallel to one another. In alternative embodiments, axes $A_5$ and $A_6$ may be oriented at oblique angles with respect to first longitudinal axis $L_1$ and/or each other.

Figure 3:
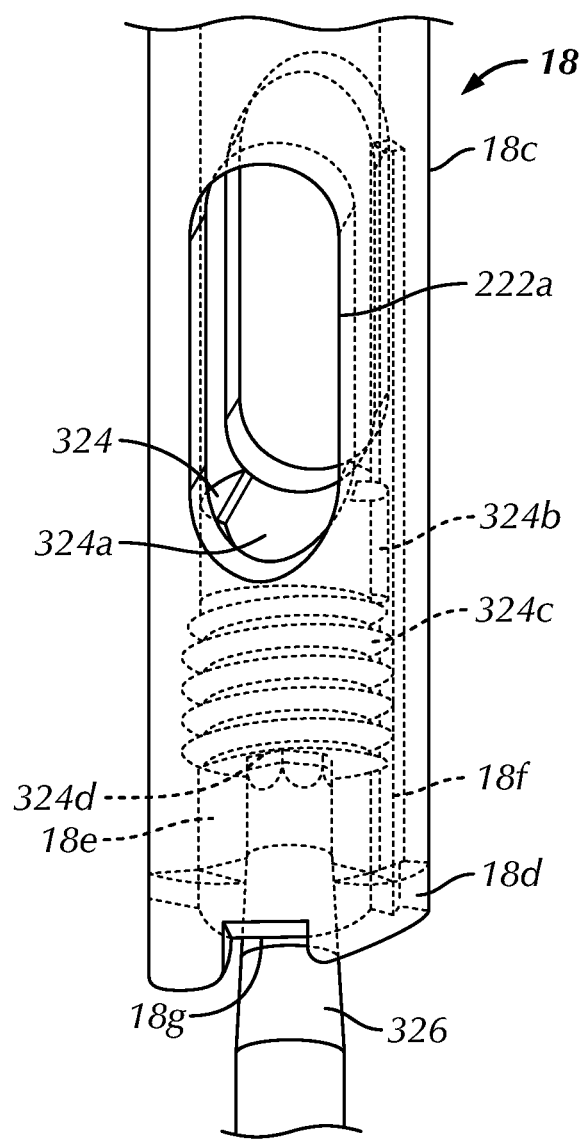
FIG. 3 is a partial perspective view of a distal portion of the nail of FIG. 1A illustrating the use of a compression screw in accordance with an exemplary embodiment of the present invention.
Figure 4:
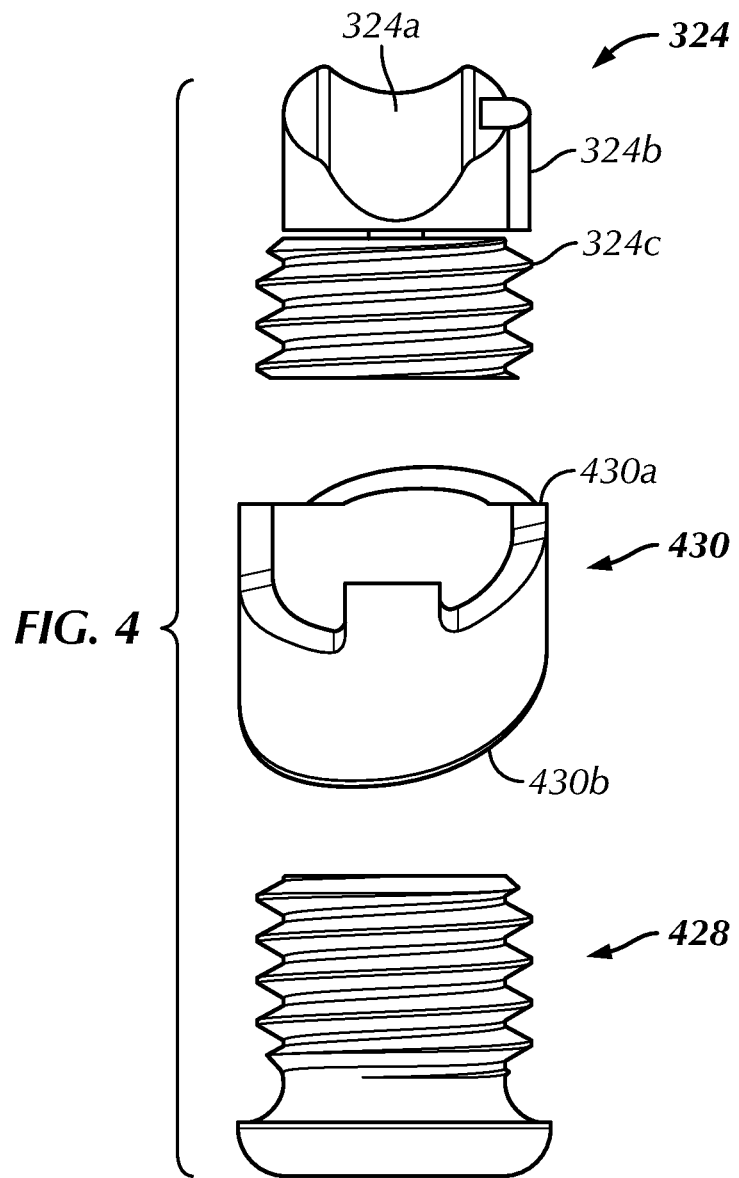
FIG. 4 is an exploded perspective view of the compression screw of FIG. 3 and end caps for use with the ankle fusion device of FIG. 1A.

Referring to FIGS. 3 and 4, in embodiments with elongated fasteners holes 222a and/or 222b, nail 18 may include a compression mechanism to move two or more of calcaneus 12, talus 14 and tibia 16 closer together. To facilitate compression, in one embodiment, nail 18 includes a bore 18e extending proximally from distal end 18d along second longitudinal axis $L_2$. In one embodiment, bore 18e is at least partially threaded. Ankle fusion device 10 may include a compression screw 324. In one embodiment, compression screw 324 is configured to be received in bore 18e and translate therein along second longitudinal axis $L_2$. In one embodiment, compression screw 324 includes an engagement portion 324a having a concave surface configured to contact first fastener 20a when first fastener 20a is received in first fastener hole 222a. In one embodiment, engagement portion 324a includes a projection 324b extending into a groove 18f in the bore 18e to prevent the engagement portion 324a from rotating about the second longitudinal axis $L_2$ as the engagement portion 324a translates proximally up bore 18e. In an alternative embodiment, bore 18e includes a projection that is received in a corresponding groove in engagement portion 324a.

The compression screw 324 includes a threaded portion 324c attachable to engagement portion 324a. Threaded portion 324c includes threads configured to engage the threads of bore 18e. In one embodiment, threaded portion 324c is rotatably attached to engagement portion 324a. In one embodiment, threaded portion 324c includes an engagement member 324d such as, for example a hexagon socket or slot, for mating with a screw driver tool 326. As threaded portion 324c is rotated, compression screw 324 advances proximally through bore 18e and translates first fastener 20c proximally (e.g., across first fastener hole 222a). Since first fastener 20a is fixed relative to calcaneus 12 and at least one of third and fourth fasteners 20c, 20d keep nail 18 from being pulled distally, advancing compression screw 324 moves calcaneus 12 proximally toward talus 14. Similarly, if second fastener hole 222b is elongate, advancing compression screw 324 proximally moves talus 14 toward tibia 16. If both first and second fastener holes 222a, 222b are elongate, advancing compression screw 324 proximally moves both calcaneus and talus toward tibia 16 and compresses all three bones together. In one embodiment, bore 18e extends entirely through distal portion 18c. In one embodiment, bore 18e extends substantially through the entire nail 18 such that nail 18 is generally hollow. In some embodiments, bore 18e extends at least partially through distal portion 18c. In an alternative embodiment, bore 18e extends only through distal portion 18c that is distal to first fastener hole 222a.

Referring to FIGS. 3 and 4, ankle fusion device 10, includes, in one embodiment, an end cap screw 428 for closing bore 18e after implantation and compression. In one embodiment, end cap screw 428 is threaded for engagement of the threads in bore 18e. In an alternative embodiment, end cap screw 428 is not threaded and instead snap fits into bore 18e.

In some embodiments, distal end 18d of nail 18 includes a groove or step 18g for engaging and orienting tools about and relative to second longitudinal axis $L_2$ as described in further detail below. In such embodiments, ankle fusion device 10 may include an end cap sleeve 430. End cap sleeve 430 includes one or more projections 430a on a proximal end that are configured to align with groove 18g and an end surface 430b on a distal end that forms the distal most end of ankle fusion device 10. In one embodiment, end surface 430b is configured to be substantially flush with the surrounding calcaneus 12 and with the end cap screw 428, proximate the end of bore 18e.

In some embodiments, in order to insert nail 18 into the calcaneus 12, talus 14 and tibia 16, a path is created, e.g., by advancing (e.g., drilling) a hole proximally starting from the bottom of calcaneus 12. Referring to FIGS. 5-12, in some embodiments, one or more guidewires are inserted through the calcaneus 12, talus 14 and tibia 16 to fix reference axes for forming a path for nail 18.

Figure 5:
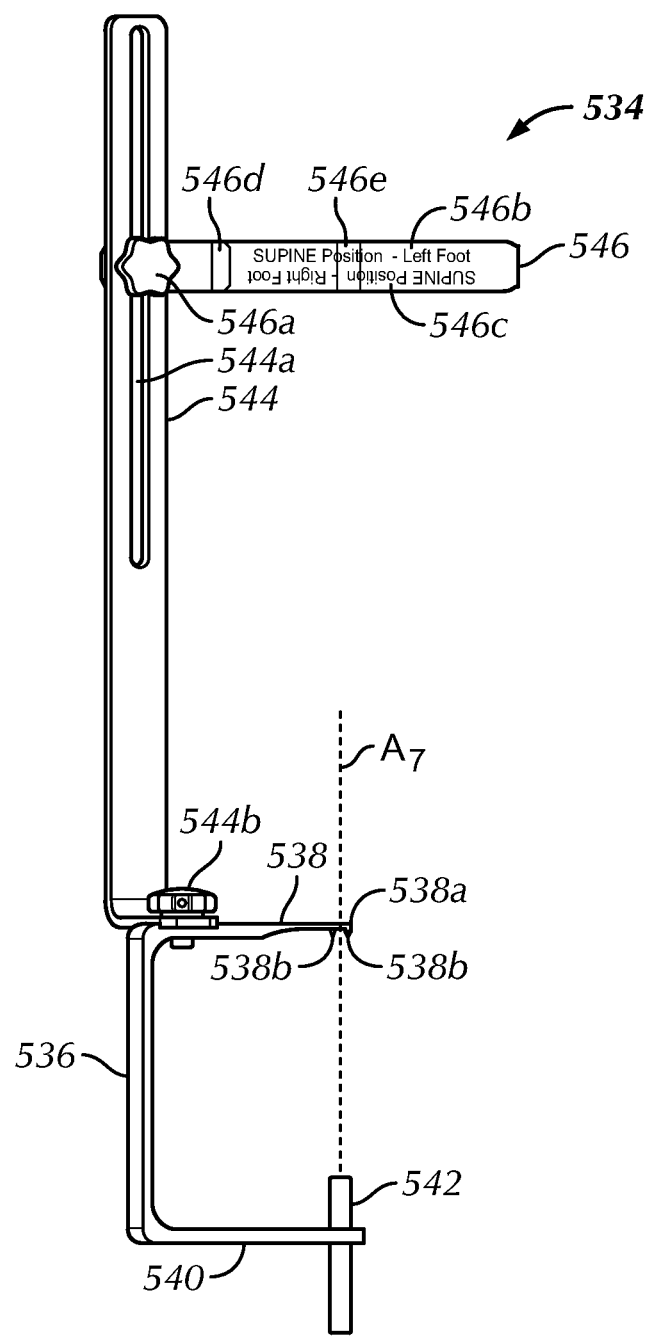
FIG. 5 is a posterior perspective view of a guidewire targeting device in accordance with an exemplary embodiment of the present invention.

Referring to FIG. 5, in some embodiments, a guidewire targeting device 534 is used in implanting ankle fusion device 10. The guidewire targeting device 534 may eliminate the need for less accurate freehand guidewire insertion techniques that are typically used to install an ankle arthrodesis. Guidewire targeting device 534 may use the orientation of the patient's anatomy (e.g., tibia 16, talus 14 and/or foot) to position at least one cutting apparatus (e.g., guidewire 1060) up through calcaneus 12, talus 14 and tibia 16 (see FIG. 10). In one embodiment, guidewire targeting device 534 is configured to account for the posterolateral bend of nail 18 as described above and sets the proper orientation for the drilling and placement of nail 18.

In one embodiment, guidewire targeting device 534 includes a frame 536 for at least partially surrounding the calcaneus 12 and talus 14. In one embodiment, frame 536 includes a target arm 538 having a guidewire target 538a configured and dimensioned to be inserted between talus 12 and tibia 16 proximate a talar dome 14a (see FIGS. 8c and 9) of talus 14. In one embodiment, first sleeve arm 540 is positioned distally from calcaneus 12 when the guidewire target 538a is inserted between talus 14 and tibia 16 proximate talar dome 14a. In one embodiment, guidewire target 538a is a semi-circular indentation in the distal end of target arm 538. In alternative embodiments, guidewire target 538a includes a marker that is visible using an imaging device such as but not limited to a radio-marker that is visible using an imaging device and/or a guide such as a slot, a hole or a projection. In one embodiment, target arm 538 includes one or more downwardly extending projections 538b used to aid in aligning guidewire target 538a with a center or apex 14b of talar dome 14a. In one embodiment, projections 538b include a pair of projections 538b positioned on either side of guidewire target 538a. In one embodiment, the distal end of target arm 538 is thinner than the remainder of the frame 536 such that target arm 538 fits more easily between talus 14 and tibia 16 while maintaining the strength of the remainder of frame 536.

In order to align a first guidewire axis $A_7$ with the guidewire target 538a, in one embodiment, frame 536 includes a first sleeve arm 540. In one embodiment, first sleeve arm 540 includes a proximal side facing towards target arm 538 and a distal side opposite the proximal side. In one embodiment, frame 536 is substantially C-shaped. In one embodiment, frame 536 is bent or at least arcuate such that target arm 538 extends above talar dome 14a while first sleeve arm 540 extends under calcaneus 12. In one embodiment, target arm 538 and first sleeve arm 540 are substantially parallel. In one embodiment, first sleeve arm 540 includes a first guidewire sleeve 542. In one embodiment, first guidewire sleeve 542 is integral with first sleeve arm 540. In one embodiment, first guidewire sleeve 542 is detachable from first sleeve arm 540. In one embodiment, first guidewire sleeve 542 is positioned at or proximate a free end of first sleeve arm 540. In one embodiment, at least a portion of first guidewire sleeve 542 extends from the proximal side of first sleeve arm 540. In one embodiment, at least a portion of first guidewire sleeve 542 extends from the distal side of first sleeve arm 540. In one embodiment, first guidewire sleeve 542 extends from the proximal side and the distal side of first sleeve arm 540. In one embodiment, first guidewire sleeve 542 is fixed in position relative to guidewire target 538a. In one embodiment, a central longitudinal axis of first guidewire sleeve 542 is configured to co-axially align with first guidewire axis $A_7$. In one embodiment, first guidewire sleeve 542 is fixed in position relative to target arm 538. In one embodiment, first guidewire sleeve 542 is radially disposed about first guidewire axis $A_7$. In one embodiment, first guidewire axis $A_7$ is aligned with guidewire target 538a.

In order to co-axially align first guidewire axis $A_7$ with first longitudinal axis $L_1$, guidewire targeting device 534 may be aligned with and/or attached to at least one anatomical feature of the patient. In one embodiment, the at least one anatomical feature is tibia 16. In one embodiment, guidewire targeting device 534 includes a tibial member or alignment guide 544. In one embodiment, tibial alignment guide 544 is engaged with frame 536 and is configured to extend proximally therefrom along a longitudinal axis substantially parallel to the first guidewire axis $A_7$. In one embodiment, tibial alignment guide 544 is attached to target arm 538. In one embodiment, tibial alignment guide 544 is moveably attached to frame 536 using a fastener 544b. In one embodiment, tibial alignment guide 544 is moveably attached to frame 536 using a star grind fastener such that tibial alignment guide 544 may be positioned relative to tibia 16 and frame 536 may be independently rotated about first longitudinal axis $L_1$ and then locked in position relative to tibial alignment guide 544 once in the appropriate position. In one embodiment, the position of frame 536 relative to tibial alignment guide 544 is adjustable but generally set by the surgeon prior to attaching to the patient. In one embodiment, the position of frame 536 relative to tibial alignment guide 544 is adjustable once guidewire targeting device 534 has been attached to the patient. In one embodiment, the position of frame 536 relative to tibial alignment guide 544 is radially adjustable. In alternative embodiments, transverse member 546 is fixed to frame 536.

To further aid in positioning guidewire targeting device 534, tibial alignment guide 544 may include a transverse member 546. In some embodiments, transverse member 546 extends generally perpendicularly from tibial alignment guide 544. In one embodiment, transverse member 546 is configured to have a curvature about first guidewire axis $A_7$, such that the transverse member 546 wraps at least partially around the leg during use. In one embodiment, the transverse member 546 is positionable at different locations along a length of tibial alignment guide 544 to aid in aligning first guide wire axis $A_7$ with first longitudinal axis $L_1$ during use as described further below. In one embodiment, tibial alignment guide 544 includes a longitudinal slot 544a extending at least partially along a length of tibial alignment guide 544. In one embodiment, transverse member 546 includes a fastener 546a such as a screw knob that extends through longitudinal slot 544a. In alternative embodiments, transverse member 546 may be movable attached to or fixedly attached but moveable relative to tibial alignment guide 544 in any manner. In one embodiment, instead of a longitudinal slot 544a, tibial alignment guide 544 includes a plurality of holes. In an alternative embodiment, transverse member 546 is fixed relative to or integral with tibial alignment guide 544.

In one embodiment, transverse member 546 is bendable or conformable such that the surgeon can shape transverse member 546 to the shape of the patient's leg. In one embodiment, transverse member 546 includes an attachment member (not shown) such as, for example, a Velcro strap and/or elastic band that is configured to attached to the patient's leg. In one embodiment, frame 536 and/or transverse member 546 may be attached to tibial alignment guide 544 in the opposite facing direction for use with the right ankle.

In one embodiment, frame 536 and/or tibial alignment guide 544 includes indicia (not shown) to indicate the proper orientation of or connection between components of guidewire targeting device 534 for the left and right foot. In one embodiment, frame 536 and/or transverse member 546 includes indicia (not shown) to indicate the general position frame 536 should be oriented to tibial alignment guide 544 depending on the position of the patient during surgery. In one embodiment, transverse member 545 includes indicia 546b, 546c to indicate the proper orientation for the left and right foot. In the embodiment illustrated, transverse member 546 is shaped for use when the patient is in the supine position. In some embodiments, a differently shaped transverse member 546 may be provided for patients in the prone position. In alternative embodiments, a single transverse member 546 is provided and frame 536 may be attached to tibial alignment guide 544 in a radial orientation relative to tibial alignment guide 544 depending on the position of the patient.

In one embodiment, transverse member 546 includes a first alignment member 546d for aligning with the first longitudinal axis $L_1$ and/or first guidewire 1060 as described further below. In one embodiment, transverse member 546 includes a second alignment member 546e for aligning with first longitudinal axis $L_1$ and/or first guidewire 1060. In one embodiment, first and/or second alignment members 546d, 546e are configured and positioned to intersect with a plane aligned with the first guidewire axis $A_7$. In one embodiment, first and second alignment members 546d, 546e include indents or bends in the transverse member 546. In one embodiment, first and second alignment members 546d, 546e include one or more projections and/or grooves in the transverse member 546. In alternative embodiments, first and second alignment members 546d, 546e include a marker that is visible using an imaging device such as but not limited to a radio-marker that is visible using an imaging device. In some embodiments, the horizontal thickness of first and second alignment members 546d, 546e is generally equal to a thickness of first guidewire 1060. In one embodiment, first alignment member 546d is positioned along the length of transverse member 546 such that first alignment member 546d aligns with first longitudinal axis $L_1$ from a lateral view of tibia 16 and second alignment member 546e is positioned along the length of transverse member 546e such that second alignment member 546e aligns with first longitudinal axis $L_1$ from an anterior view of tibia 16. In one embodiment, aligning first and second alignment member 546e with first longitudinal axis $L_1$ from two directions helps to ensure that tibial alignment guide 534 is substantially parallel with first longitudinal axis $L_1$.

Figure 6:
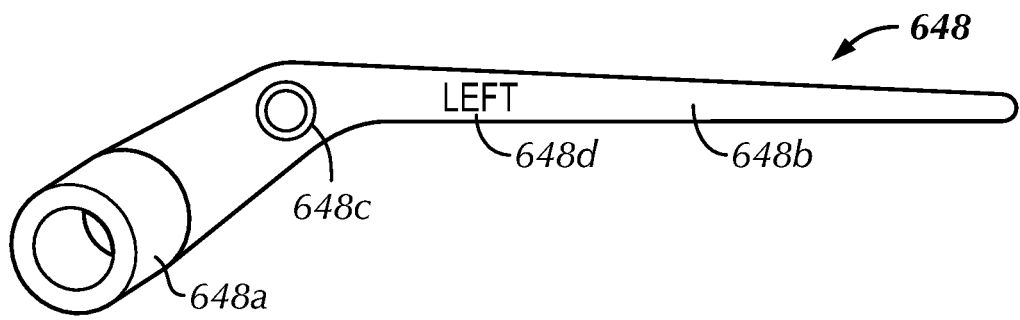
FIG. 6 is a ventral or bottom plan view of a guidewire template in accordance with an exemplary embodiment of the present invention.
Figure 7:
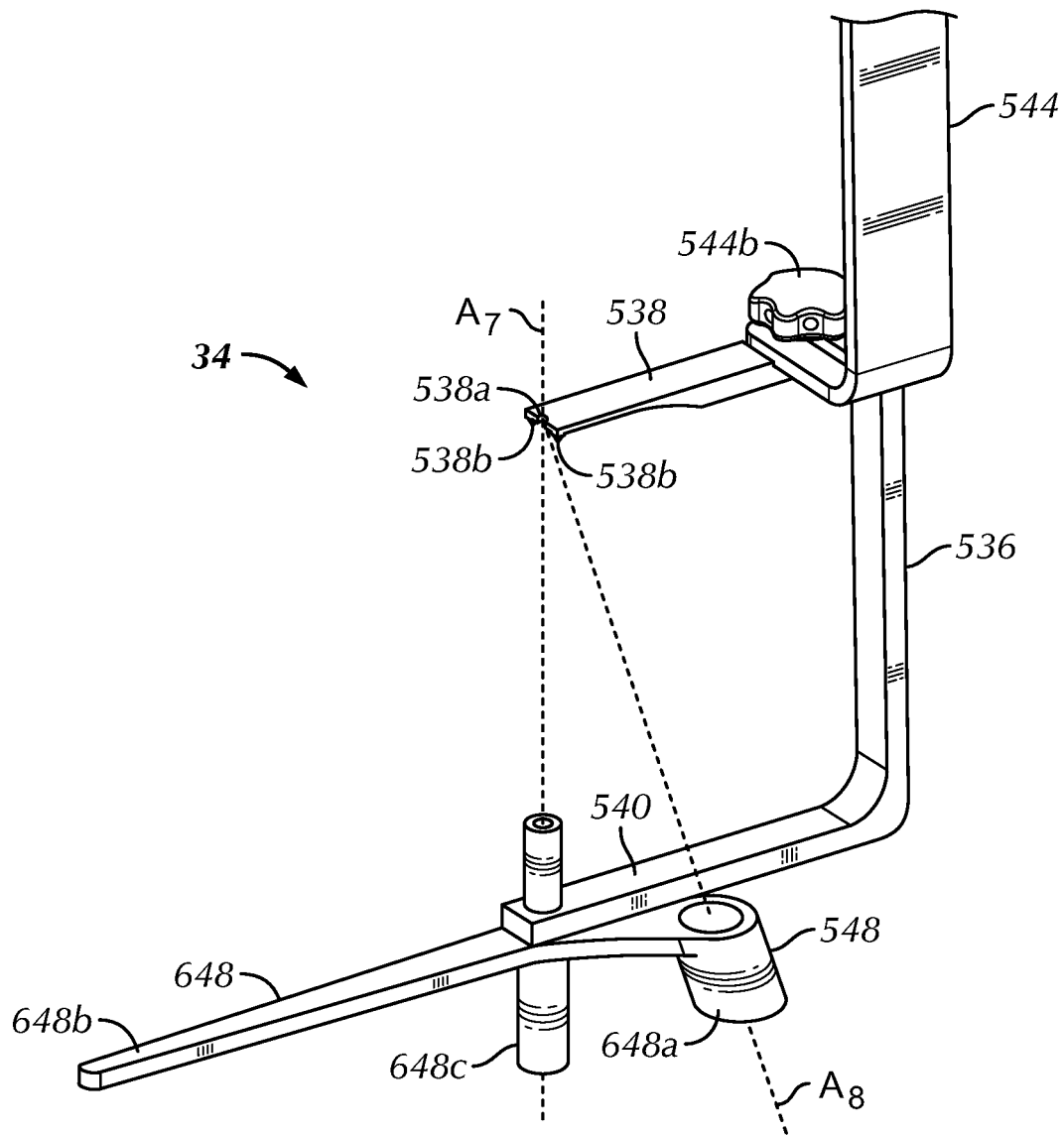
FIG. 7 is a perspective view of the guidewire targeting device of FIG. 5 in use with a guidewire template of FIG. 6 showing first and second guidewire axes.

Referring to FIGS. 6 and 7, guidewire targeting device 534 may include a second guidewire template 648 for use with a second guidewire 1262. Second guidewire template 648 is configured to align a second guidewire axis $A_8$ with the guidewire target 538a. Second guidewire template 648 includes a second position sleeve 648a radially disposed about a second guidewire axis $A_8$. In one embodiment, first guidewire sleeve 542 is used to co-axially align first guidewire axis $A_7$ with first longitudinal axis $L_1$ and second position sleeve 648a is used to co-axially align second guidewire axis $A_8$ with the desired position of second longitudinal axis $L_2$. In one embodiment, guidewire targeting device 534 is configured to position second longitudinal axis $L_1$. In one embodiment, guidewire targeting device 534 is configured to align first longitudinal axis $L_1$ with the central longitudinal axis of tibia 16 and guidewire targeting device 534 is configured to position second longitudinal axis $L_2$ in a preselected orientation with respect to the position of first longitudinal axis $L_1$. In one embodiment, the preselected orientation is based on the shape of nail 18.

Second guidewire template 648 (see, e.g., FIG. 6) may be integral, moveable and/or detachable with frame 536. In one embodiment, second guidewire template 648 is removably attached to first sleeve arm 540. In one embodiment, second guidewire template 648 is positioned distally with respect to frame 536. In one embodiment, second guidewire template 648 is configured to abut the distal side of first sleeve arm 540. In one embodiment, second guidewire template 648 is positioned such that at least a portion of first sleeve arm 540 is located between second guidewire template 648 and target arm 538. In other embodiments, at least a portion of second guidewire template 648 is positioned between target arm 538 and first sleeve arm 540. In one embodiment, second guidewire template 648 includes an attachment sleeve 648c. In one embodiment, attachment sleeve 648c is configured and dimensioned to engage with at least a portion of first guidewire sleeve 542. In one embodiment, attachment sleeve 648c is configured to engage with a portion of first guidewire sleeve 542 that extends from the distal side of first sleeve arm 540. In one embodiment, attachment sleeve 648c is compression fit over first guidewire sleeve 542 such that attachment sleeve 648c is moveable with respect to first guidewire sleeve 542 but remains in place relative to first guidewire sleeve 542 after first guidewire sleeve 542 is positioned and released by the surgeon. In one embodiment, attachment sleeve 648c snap fits onto first guidewire sleeve 542 such that movement of attachment sleeve 648c is retained along first guidewire axis $A_7$ but is free to rotate about first guidewire axis $A_7$. In one embodiment, second position sleeve 648a is configured to rotate about first guidewire axis $A_7$. In one embodiment, second position sleeve 648a is translatable along an arc about first guidewire axis $A_7$.

In one embodiment, second position sleeve 648a is configured to be a retainer for receiving and aligning a second guidewire sleeve 1252 (see, e.g., FIG. 12) along second guidewire axis $A_8$. In an alternative embodiment, second guidewire sleeve 1252 is integral with second position sleeve 648a.

Second guidewire template 648 may include an alignment arm 648b for positioning second guidewire axis $A_8$ relative to first longitudinal axis $L_1$ by aligning alignment arm 648b relative to an anatomical feature of the patient. In embodiments where second guidewire template 648 is moveable with respect to frame 536, alignment arm 648b may be used to position second guidewire axis $A_8$ relative to first guidewire axis $A_7$ and relative to first longitudinal axis $L_1$ by aligning alignment arm 648b relative to an anatomical feature of the patient. In one embodiment, second guidewire template 648 is configured such that second guidewire axis $A_8$ is substantially aligned with guidewire target 538a and/or center 14b of talar dome 14a when alignment arm 648b is aligned with a pre-selected anatomical feature of the patient. In one embodiment, alignment arm 648b extends generally perpendicularly from first guidewire axis $A_7$. In one embodiment, the pre-selected anatomical feature aligned with the alignment arm 648b is generally perpendicular to the central axis of tibia 16 (i.e., first longitudinal axis $L_1$). In one embodiment, the preselected anatomical feature is a second metatarsal bone 1150 (see FIG. 11). In one embodiment, alignment arm 648b is aligned to be substantially parallel with second metatarsal 1150 to determine the position of second guidewire axis $A_8$. In alternative embodiments, the pre-selected anatomical feature is any one of the elongated bones in the foot.

Figure 8A:
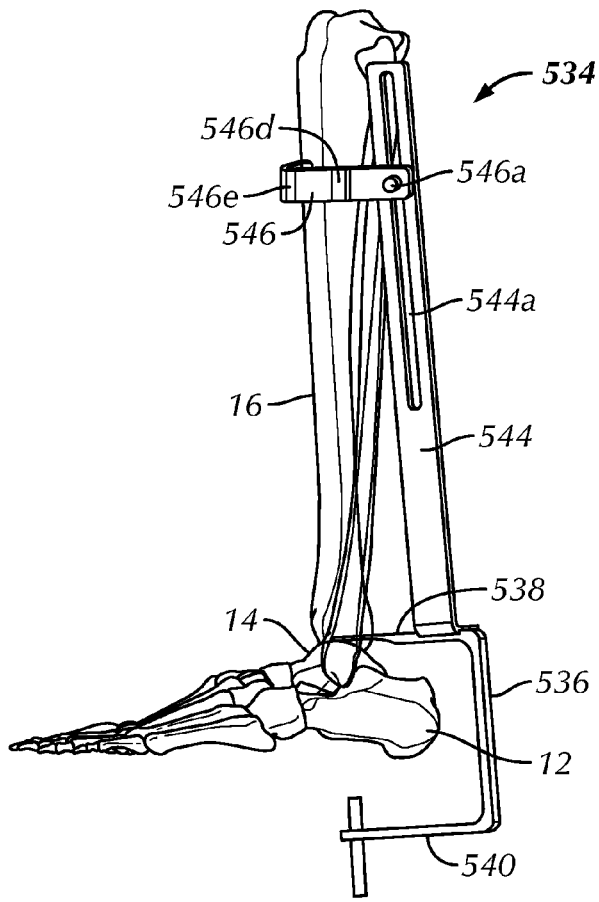
FIG. 8A is a lateral elevational view of the guidewire targeting device of FIG. 5 in use upon initial insertion.
Figure 8B:
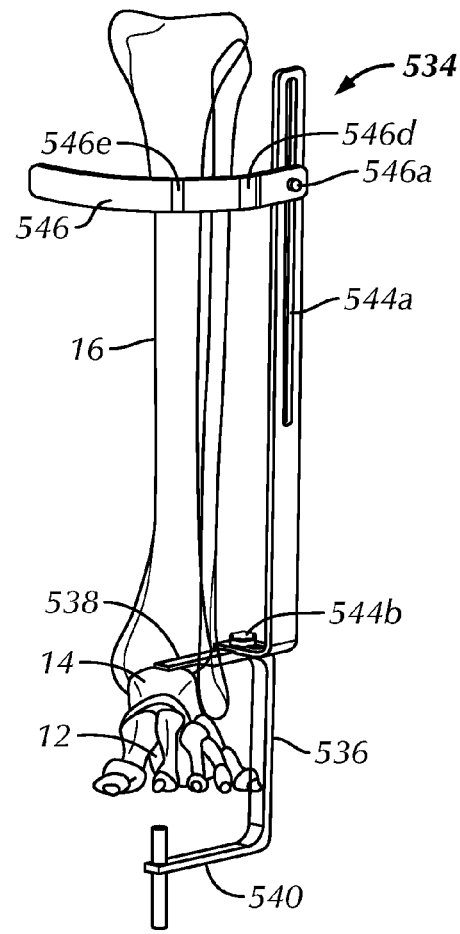
FIG. 8B is an anterior elevational view of the guidewire targeting device shown in FIG. 8A.
Figure 8C:
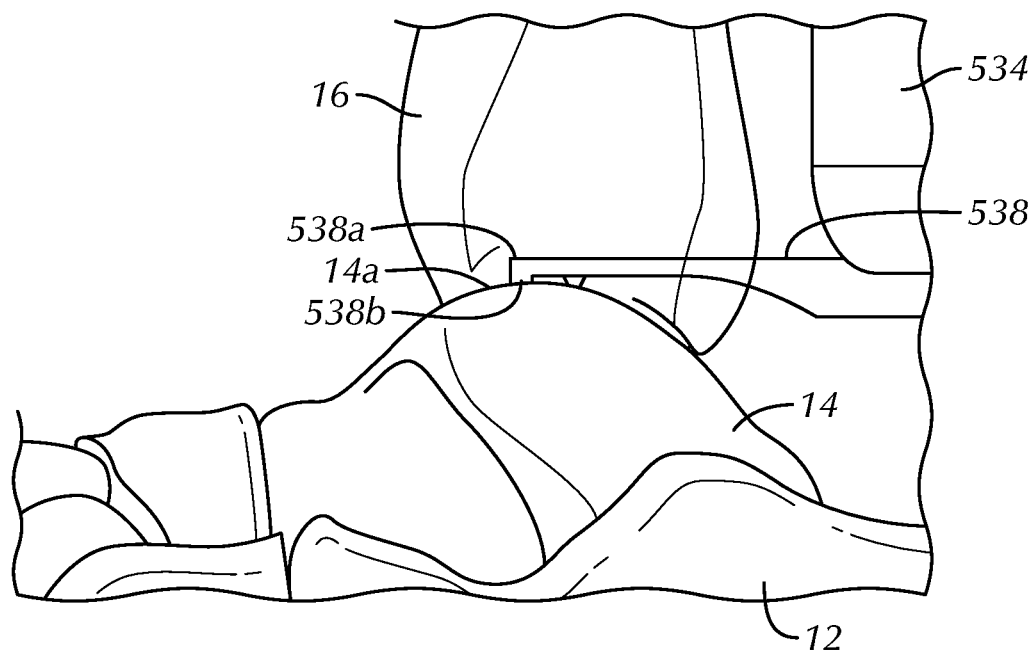
FIG. 8C is an enlarged lateral elevational view of the guidewire targeting device shown in FIG. 8A.
Figure 9:
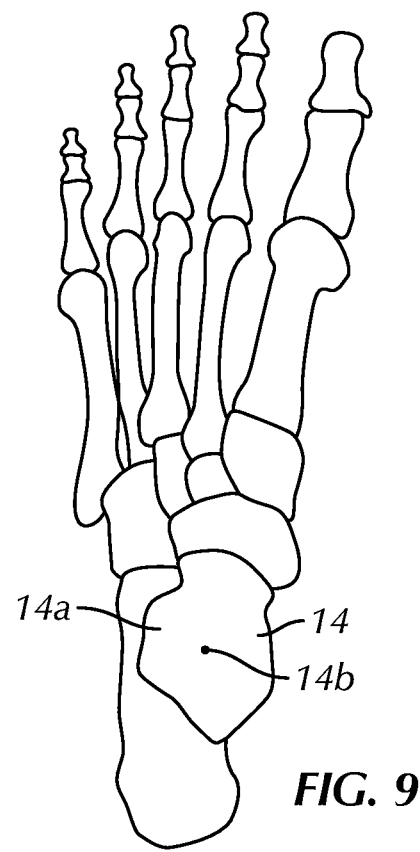
FIG. 9 is a dorsal or top plan view of a target on the talar dome of the talus.

Referring to FIGS. 8A-8B, in an exemplary embodiment in use, guidewire targeting device 534 is used to prepare the ankle for insertion of ankle fusion device 10. First and second guidewires 1060, 1262 may be used to properly align nail 18 with the patient's anatomy. In one embodiment, first guidewire 1060 is generally aligned with first longitudinal axis $L_1$ (e.g., the central longitudinal axis of tibia 16) and second guidewire 1262 is generally aligned with the position of second longitudinal axis $L_2$ once nail 18 is implanted (e.g., at an oblique angle relative to first longitudinal axis $L_1$). In one embodiment, first and second guidewires 1060, 1262 are used in order to form a cutting path corresponding to the bent shape of nail 18 using two generally straight lines. In alternative embodiments, a single guidewire may be used if the guidewire bends during insertion or if the foot is positioned such that the paths for the first and second longitudinal axes $L_1$, $L_2$ are co-axially aligned during insertion of the guidewire. In one embodiment, the use of first and second guidewires 1060, 1262 allows for more accurate alignment with first and second longitudinal axes $L_1$, $L_2$ since first guidewire 1060 is used to co-axially align with first longitudinal axis $L_1$ using anatomical features such as the talar dome 14a and the tibia 16 and the second wire 1262 can be positioned relative to the first guidewire 1062 (or the path created by the first guidewire).

Before beginning the procedure, the position of the patient may be determined based on the type of arthrodesis procedure performed and the discretion of the surgeon. In one embodiment, the patient is placed in the prone position. In another embodiment, the patient is placed in the supine position. In some embodiments, for example, with a patient in the prone position, guidewire targeting device 534 is placed in the posterior (not shown) or posterolateral position (the position shown in the exemplary embodiment of FIGS. 8A-12). In alternative embodiments, for example, where a patient is in the supine position, the guidewire targeting device 534 may be placed in the anterolateral position.

Referring to FIGS. 8A-8C and 9, the foot may be oriented relative to tibia 16 in the position that the ankle is to be fixed in place. In one embodiment, the ankle is placed in a neutral position. In other embodiments, the ankle is placed in about 2 to about 3 degrees dorsi flexion. Once the ankle is in the desired position, guidewire target 538a is inserted between talus 14 and tibia 16. In one embodiment, guidewire target 538a is placed proximate talar dome 14a (see FIG. 9). In one embodiment, guidewire target 538a is placed proximate center 14b of talar dome 14a. In one embodiment, guidewire target 538a is positioned generally directly above center 14b of talar dome 14a. In one embodiment, center 14b of talar dome 14a is aligned with first longitudinal axis $L_1$ and the central axis of tibia 16. In one embodiment, projections 538b are positioned on either side of center 14b of talar dome 14a. In one embodiment, the position of guidewire target 538a relative to talus 14 is viewed using imaging such as fluoroscopic imaging.

In addition to positioning guidewire target 538a relative to talus 14, first guidewire sleeve 542 is positioned under calcaneus such that first guidewire axis $A_7$ generally aligns with guidewire target 538a. In one embodiment, first guidewire sleeve 542 is positioned so that first guidewire sleeve 542 aligns exactly with guidewire target 538a. In one embodiment, first guidewire sleeve 542 is positioned so that first guidewire axis $A_7$ is aligned with center 14b of talar dome 14a.

In one embodiment, tibial alignment guide 544 is used to help align the first guidewire axis $A_7$ with first longitudinal axis $L_1$ by positioning tibial alignment guide 544 substantially parallel with tibia 16. In one embodiment, first alignment member 546d and/or second alignment member 546e are aligned with first longitudinal axis $L_1$ in the lateral and anterior views, respectively, to position tibial alignment guide 544 substantially parallel with tibia 16.

In one embodiment, tibial alignment guide 544 is positioned relative to first longitudinal axis $L_1$ by sliding or otherwise positioning transverse member 546 along the length of tibial alignment guide 544 and in contact with the outer surface of the leg. In one embodiment, transverse member 546 prevents guidewire targeting device 534 from moving with respect to the patient. In one embodiment, without transverse member 546, guidewire targeting device 534 would pivot laterally and posteriorly relative to guidewire target 538a caused by the weight of guidewire targeting device 534. In one embodiment, transverse member 546 counters any pivot of guidewire targeting device 534 with respect to the guidewire target 538a. Due to the shape of the leg, in one embodiment, moving transverse member 546 along the length of tibial alignment guide 544 alters the orientation of first guidewire axis $A_7$ in a first plane until first guidewire axis $A_7$ is aligned with first longitudinal axis $L_1$. In one embodiment, the curvature of transverse member 546 keeps first guidewire axis $A_7$ aligned with first longitudinal axis $L_1$ in a second plane, the second plane being generally perpendicular to the first plane.

Figure 10:
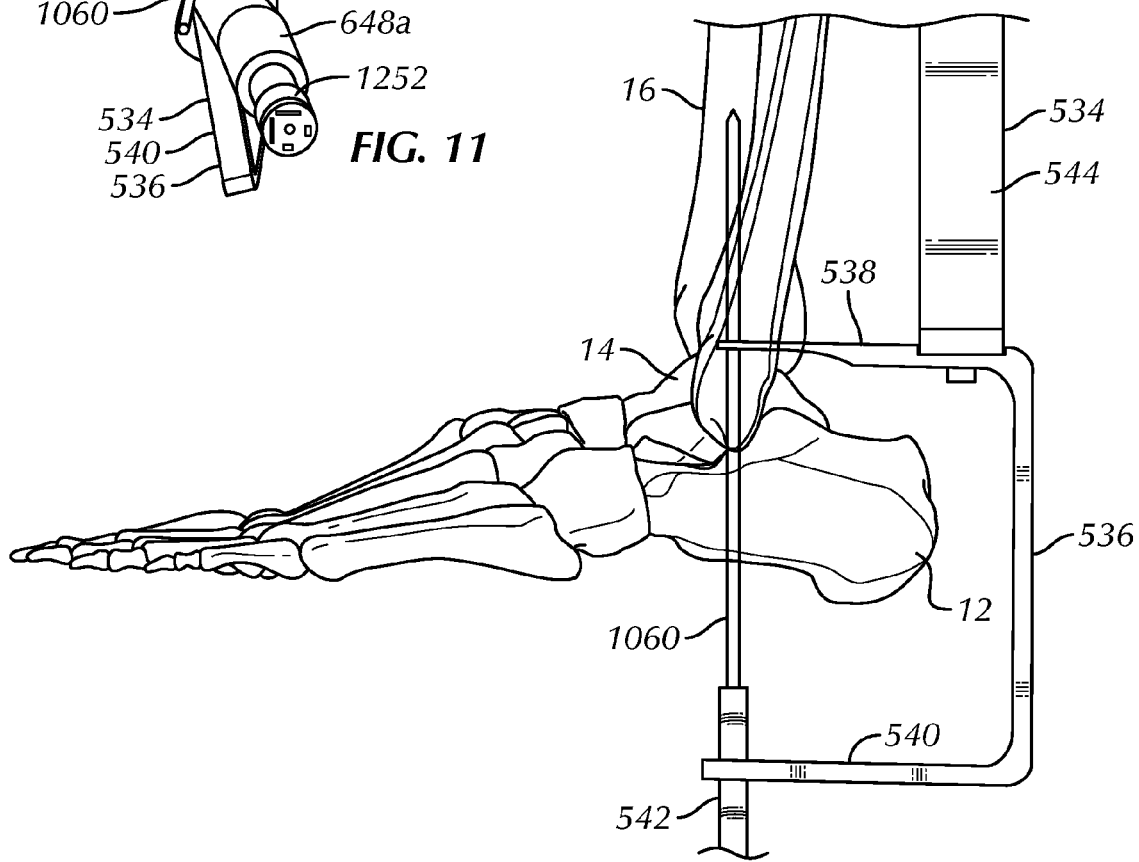
FIG. 10 is a lateral elevational view of the guidewire targeting device shown in FIG. 8A in use with a first guidewire.

Referring to FIG. 10, once first guidewire axis $A_7$ is in the desired position, a first guidewire 1060 is advanced proximally through first guidewire sleeve 542, along first guide wire axis $A_7$, through calcaneus 12 and talus 14 and into the distal end of tibia 16. In one embodiment, the placement and guidance of first guidewire 1060 is monitored using the imaging device. In one embodiment, the guidance of first guidewire 1060 is monitored using the imaging device from lateral and mortise views. In one embodiment, first guidewire 1060 is aligned with first alignment member 546d and/or second alignment member 546e in the lateral and anterior views, respectively. Advancement of the first guidewire 1060 along first guidewire axis $A_7$, in some embodiments, creates a channel in the distal end of tibia 16 substantially aligned with first longitudinal axis $L_1$.

Figure 11:
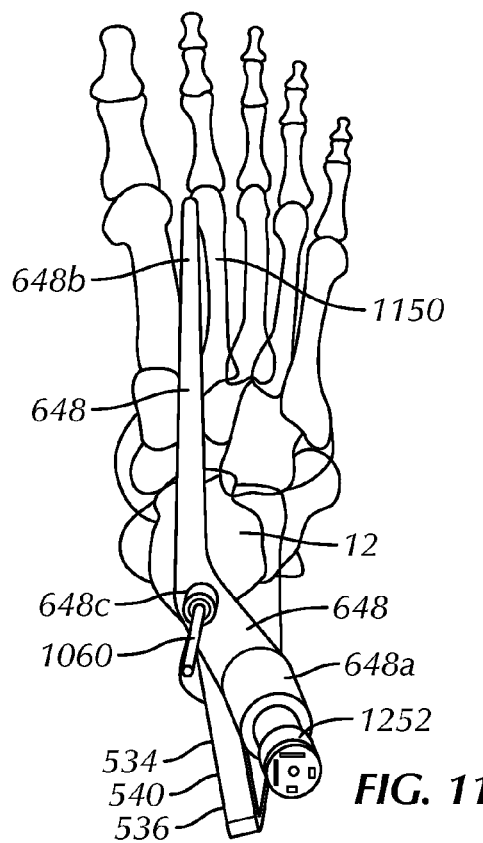
FIG. 11 is a ventral or bottom plan view of the guidewire targeting device and guidewire template of FIG. 7 in use with the first and second guidewires.

Referring to FIG. 11, if second guidewire template 648 is not already coupled with frame 536, second guidewire template 648 is attached to guidewire targeting device 534. In one embodiment, second guidewire template 648 include indicia 648d (see FIG. 6) such as the word "Left" and/or color coding to indicate the appropriate left or right foot. Once the second guidewire template 648 is attached to guidewire targeting device 534, second guidewire template 648 may be positioned relative to frame 536 and/or first guidewire axis $A_7$ by aligning alignment arm 648b with an anatomical feature of the patient such as second metatarsal 1150. Once second guidewire template 648 is in place second guidewire axis $A_8$ generally aligns with guidewire target 538a and is co-axial with where second longitudinal axis $L_2$ will be. In one embodiment, once second guidewire template 648 is in place, second guidewire axis $A_8$ generally aligns with the anterior margin of the plantar aspect of the calcaneal tuberosity equidistant from the medial and lateral wall of calcaneus 12.

Figure 12:
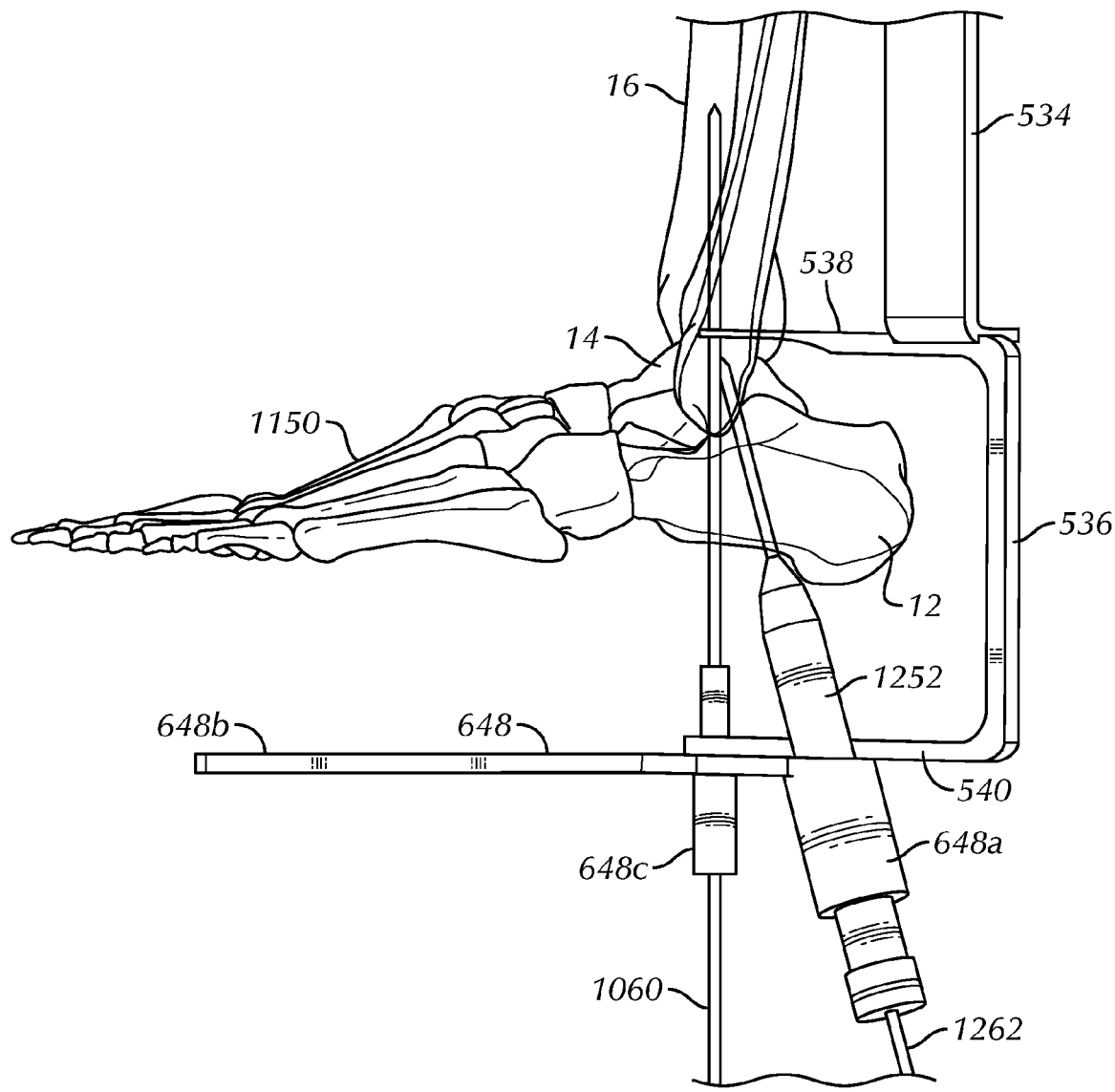
FIG. 12 is a lateral elevational view of the guidewire targeting device and guidewire template shown in FIG. 11.

Referring to FIG. 12, in one embodiment, second guidewire sleeve 1252 is inserted into second position sleeve 648a if second guidewire sleeve 1252 is not already attached. In one embodiment, second guidewire 1262 is advanced proximally through second guidewire sleeve 1252, through calcaneus 12 and talus 14 proximate the guidewire target 538a. In one embodiment, the position of second guidewire 1060 during insertion is monitored using the imaging device from lateral and mortise views.

Figure 13:
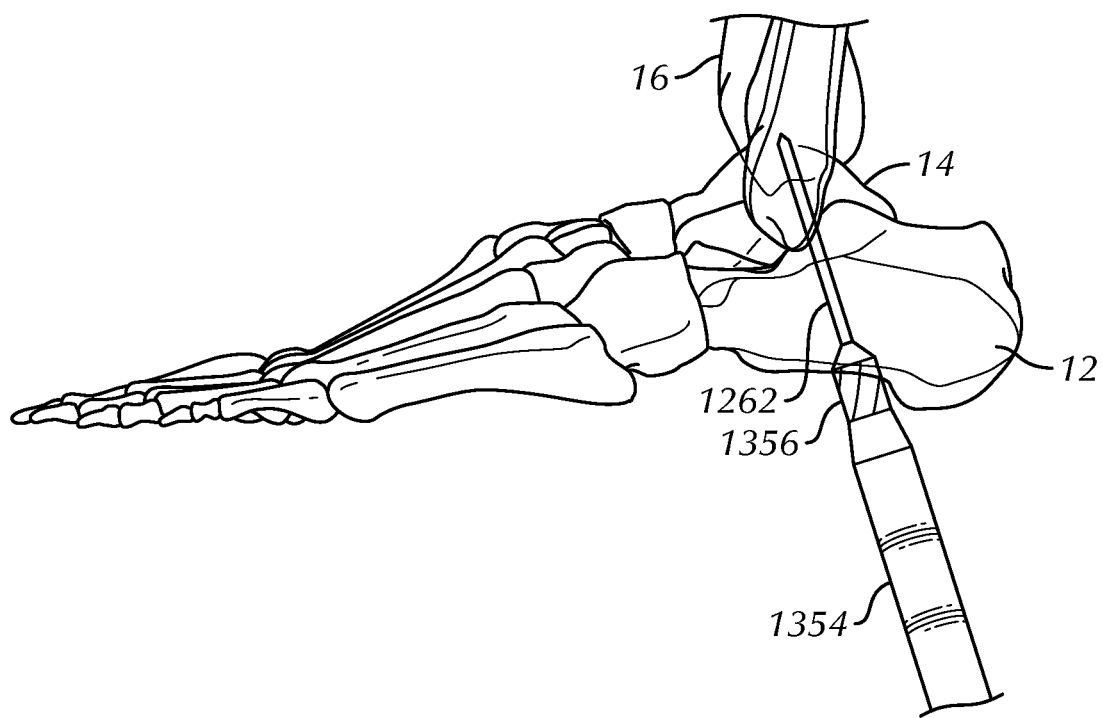
FIG. 13 is a lateral elevational view of a cannulated drill being used with the second guidewire in accordance with an exemplary embodiment of the present invention.

Referring to FIG. 13, in one embodiment, once second guidewire 1262 is in position, first guidewire 1062 and guidewire targeting device 534 are removed such that only second guidewire 1262 remains. In one embodiment, a cannulated drill 1356 is inserted over the second guidewire 1262. In alternative embodiments, the guidewire targeting device 534 is left in place, the second guidewire 1262 is removed and a drill is guided along second guidewire axis $A_8$.

Figure 14:
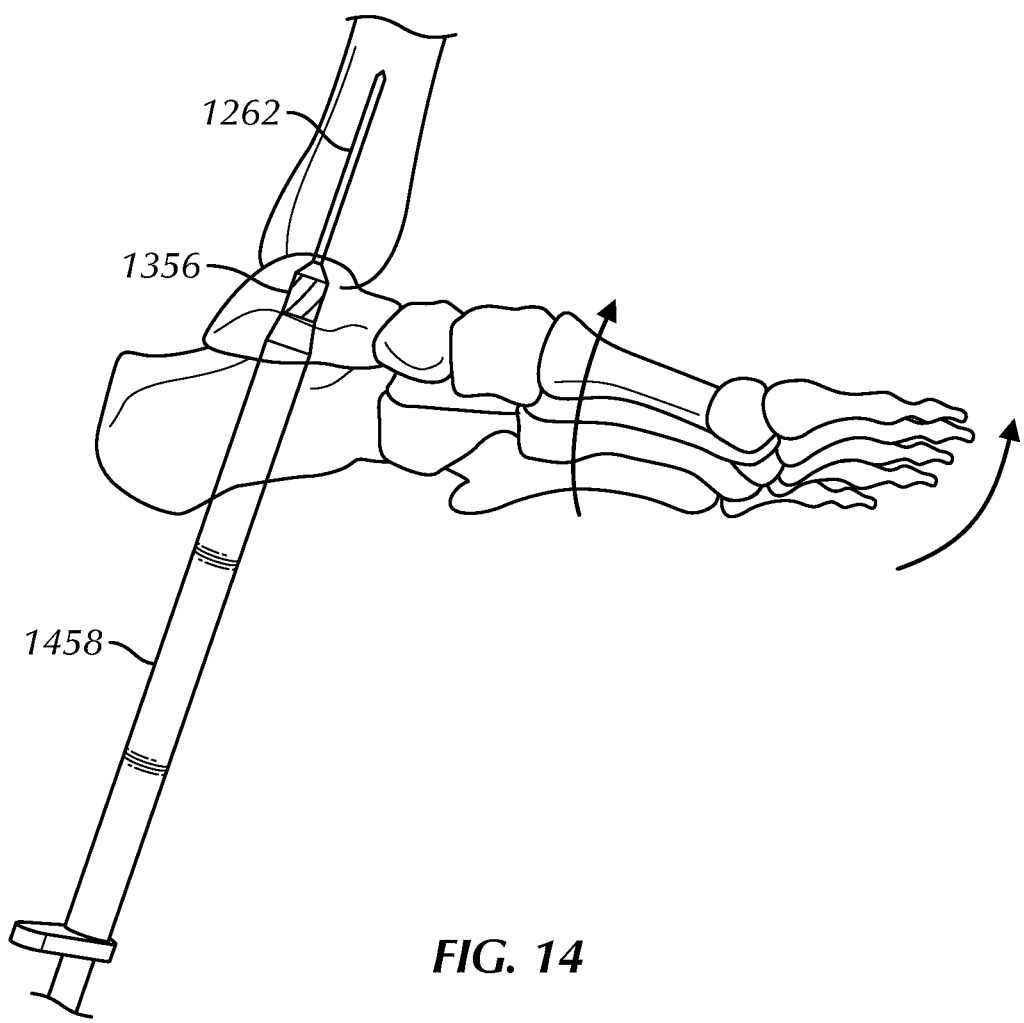
FIG. 14 is a lateral elevational view of the second guidewire and cannulated drill of FIG. 13 and a protection sleeve in accordance with an exemplary embodiment of the present invention.

Referring to FIG. 14, in one embodiment, once the cannulated drill 1356 has been advanced proximate the talar dome 14a, the foot is positioned such that second guidewire 1262 aligns with first longitudinal axis $L_1$. In some embodiments, the foot is positioned such that second guidewire 1262 is substantially aligned with a longitudinal axis of tibia 16. In some embodiments, positioning the foot includes angling the foot relative to tibia 16 such that second guidewire 1262 is substantially aligned with the channel created in the distal end of tibia 16 by the first guidewire 1060. In some embodiments, second guidewire 1262 is then advanced into the channel created in the distal end of tibia 16 by the first guidewire 1060. In one embodiment, a protection sleeve 1458 is inserted over second guidewire 1262 to aid in positioning the foot and protects the cannulated drill 1356. In one embodiment, the foot is dorsiflexed about 15 degrees and inverted 10 degrees. In one embodiment, once the foot has been repositioned, cannulated drill 1356 is advanced into tibia 16 over second guidewire 1262.

Figure 15:
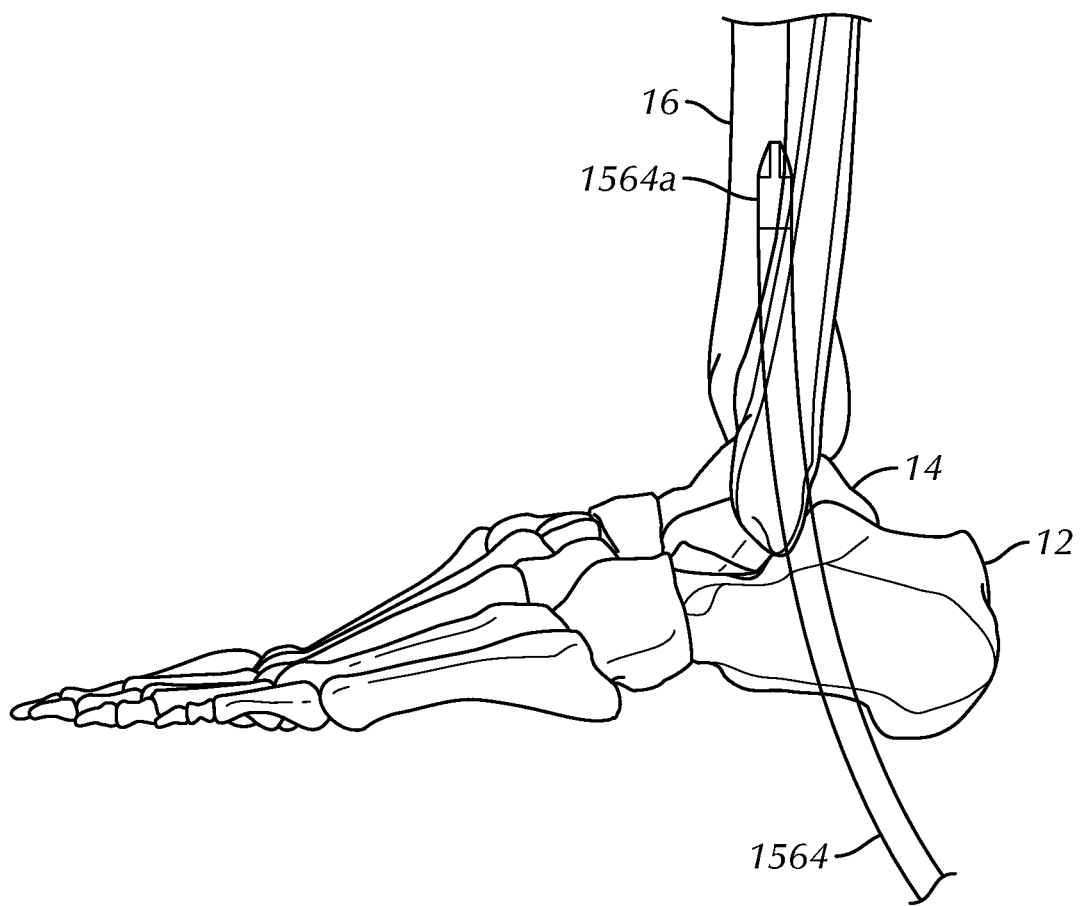
FIG. 15 is a lateral elevational view of a reamer being used in accordance with an exemplary embodiment of the present invention.

Referring to FIG. 15, in one embodiment, once the cannulated drill 1356 and second guidewire 1262 are removed, it may be desirable to ream the canal of tibia 16. In one embodiment, a reamer 1564 is inserted through the path created by the cannulated drill 1356. A narrow tibial canal may hinder insertion of nail 18. In one embodiment, progressive reaming of the tibial canal is performed using reamers having cross sectional widths of about 0.5 mm to about 1 mm larger than the diameter of nail 18.

Figure 16:
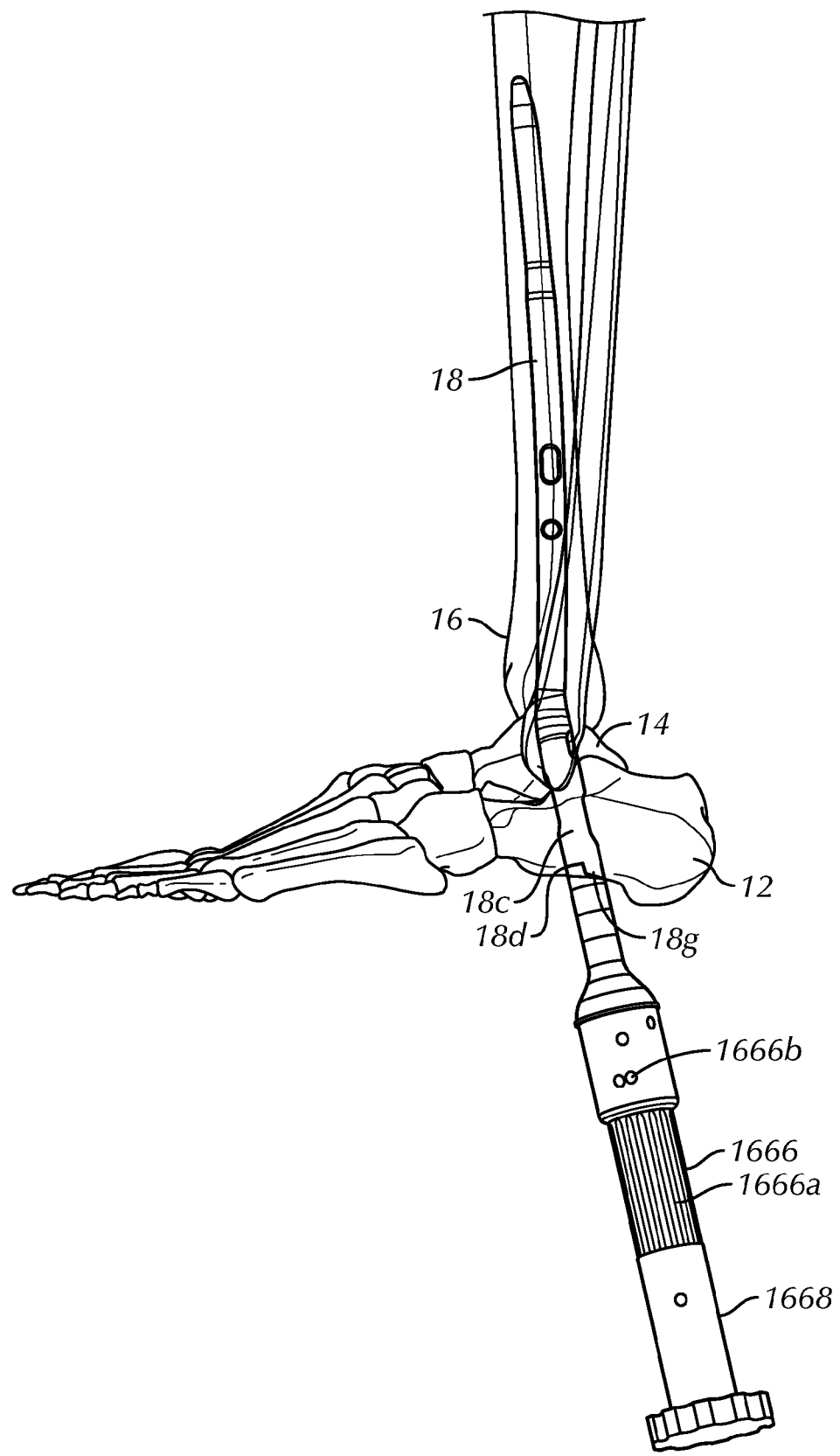
FIG. 16 is a lateral elevational view of a nail being inserted using an insertion handle in accordance with an exemplary embodiment of the present invention.
Figure 17:
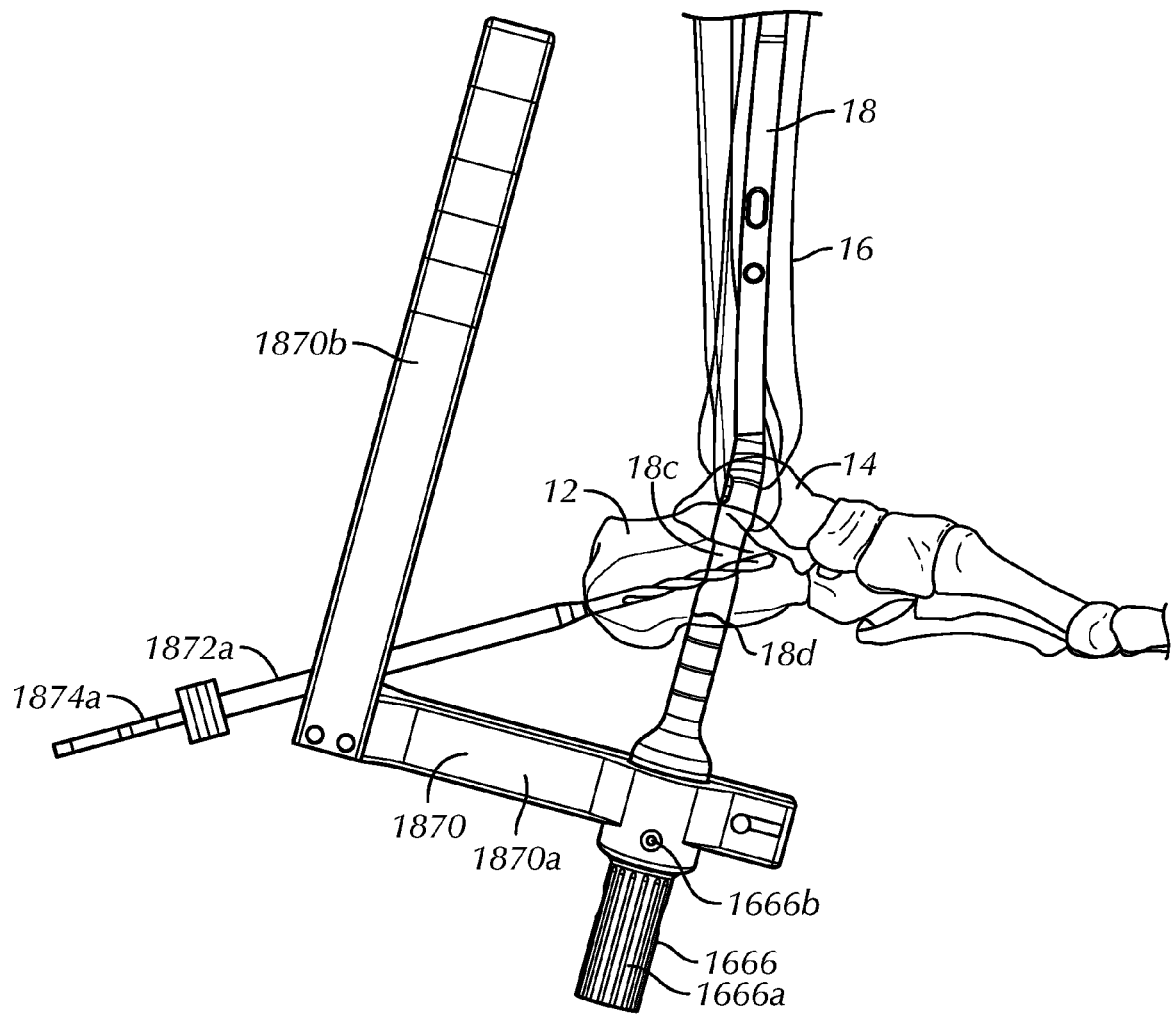
FIG. 17 is a medial elevational view of a calcaneus screw being inserted using an aiming arm in accordance with an exemplary embodiment of the present invention.
Figure 18:
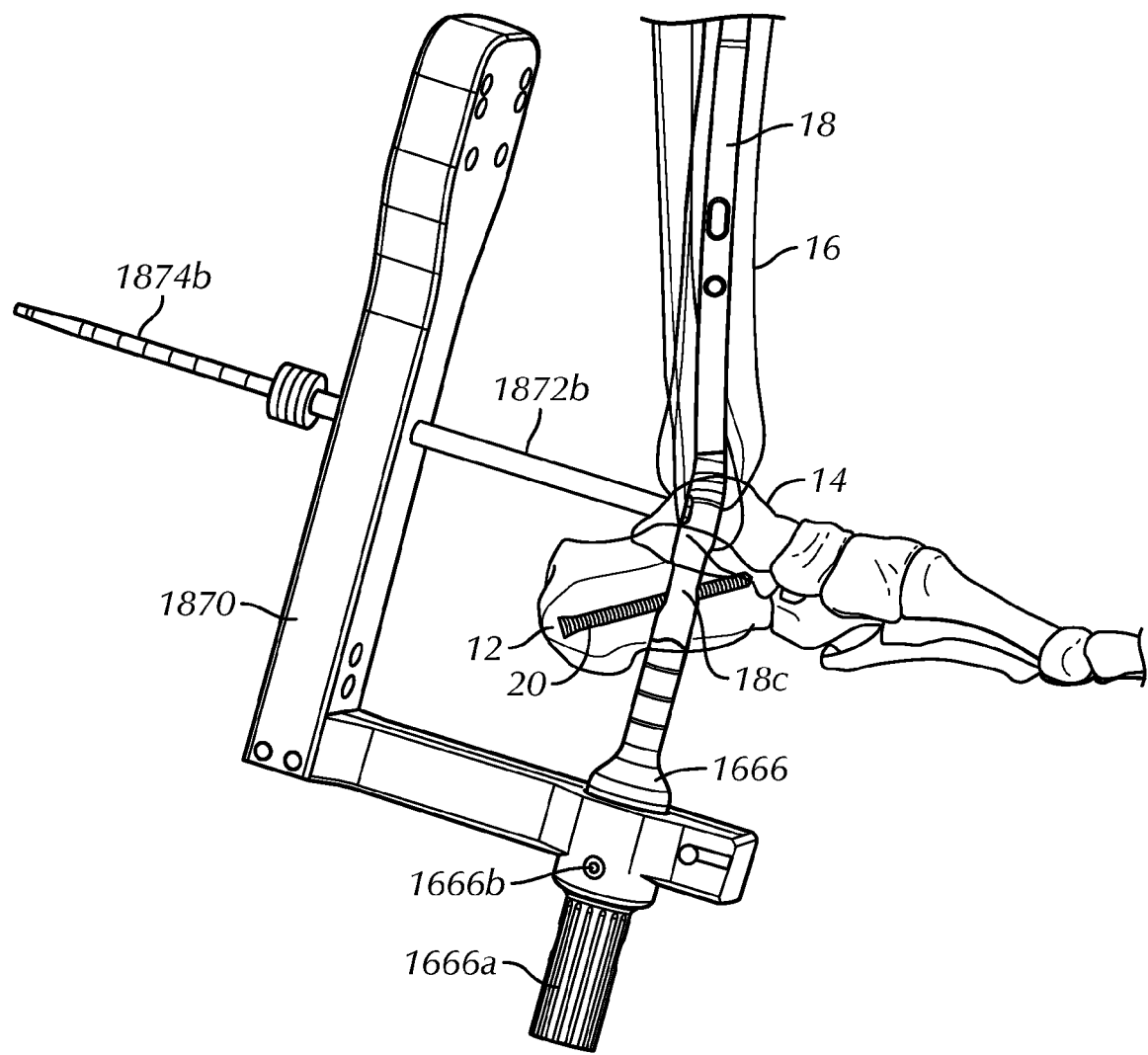
FIG. 18 is a medial elevational view of a talar screw being inserted using an aiming arm in accordance with an exemplary embodiment of the present invention.
Figure 19:
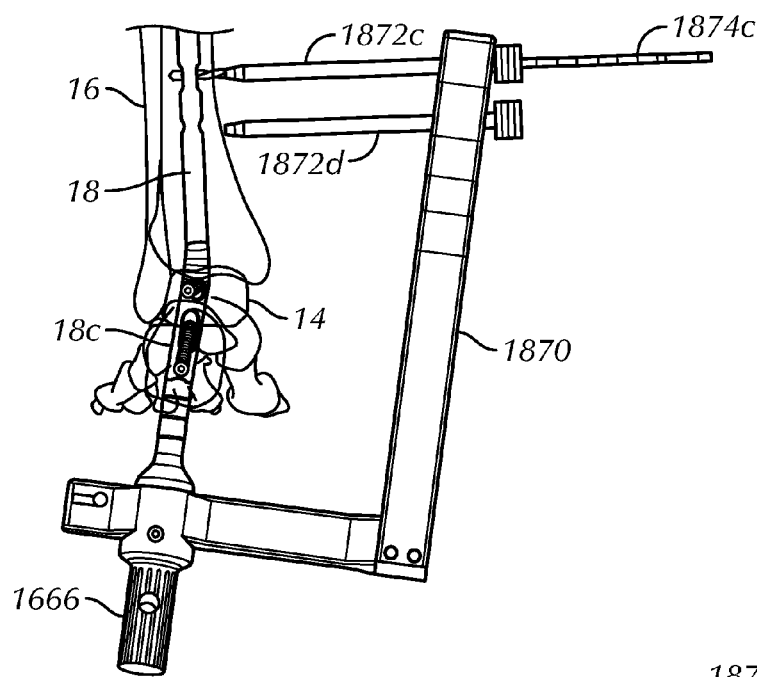
FIG. 19 is a posterior elevational view of a first tibial screw being inserted using an aiming arm in accordance with an exemplary embodiment of the present invention.
Figure 20:
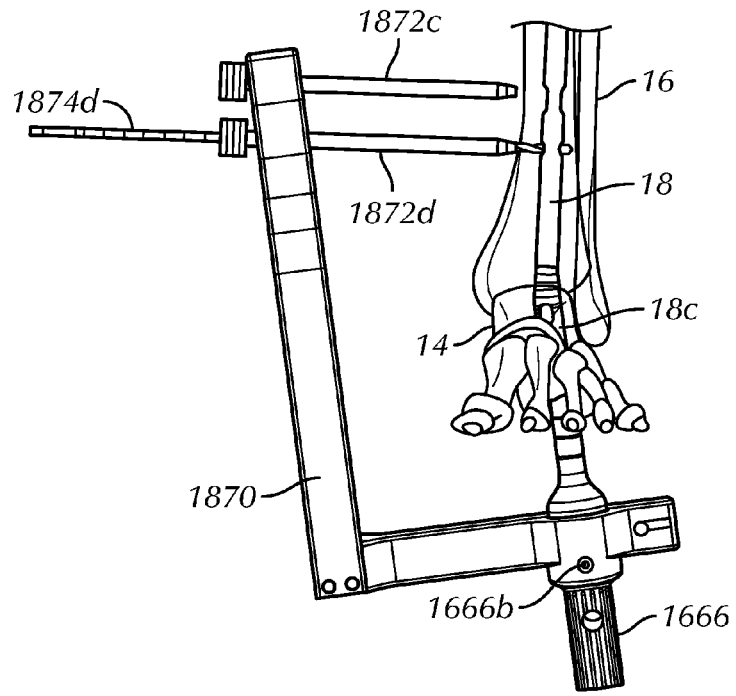
FIG. 20 is an anterior elevational view of a second tibial screw being inserted using an aiming arm in accordance with an exemplary embodiment of the present invention.

Referring to FIG. 16, once the pathway has been drilled, nail 18 may be inserted proximally through calcaneus 12 and talus 14 and into tibia 16. In one embodiment, an insertion handle 1666 is attached to distal end 18d of nail 18 to aid in insertion of nail 18. Insertion handle 1666 is configured to align with the at least one groove 18g in nail 18 so that the radial position of insertion handle 1666 is fixed relative to distal portion 18c of nail 18. In one embodiment, insertion handle 1666 is coupled to distal portion 18c of nail 18 using a threaded connecting screw (not shown) that extends upwardly into bore 18e of nail 18. In one embodiment, nail 18 is inserted as far as possible by gripping the insertion handle and pushing nail 18 upwardly across the ankle joint. In one embodiment, a driving cap 1668 may be coupled to insertion handle 1666. In some embodiments, driving cap 1668 includes a distal end surface to which a force may be applied to facilitate insertion of nail 18. Once nail 18 has been inserted, in one embodiment, nail 18 is rotated into its final position using the driving cap 1668 and insertion handle 1666. In one embodiment, placement of nail 18 is guided and monitored using the imaging device.

Referring to FIGS. 17-20, once nail 18 is in place, in some embodiments, an aiming arm 1870 is attached to insertion handle 1666. The aiming arm 1870 may be used to insert some or all of fasteners 22 relative to the position of nail 18. In one embodiment, insertion handle 1666 includes one or more longitudinally extending alignment features 1666a such a groove or projection. In one embodiment, alignment feature 1666a includes a plurality of grooves spaced circumferentially around insertion handle 1666. In one embodiment, insertion handle 1666 includes a plurality of indicia 1666b spaced radially around the insertion handle 1666. In one embodiment, indicia 1666b are used to indicate the position of aiming arm 1870 relative to first and second longitudinal axes $L_1$, $L_2$. In one embodiment, indicia 1666b includes markings such as letters that correspond to respective fasteners 20. For example, when aiming arm 1870 is aligned with first fastener hole 22a, indicia 1666b may show "C" through a viewing window in aiming arm 1870 to indicate that the hole marked "Calcaneus Screw" for calcaneus 12 should be used with the appropriate drill 1874a, drill sleeve 1872a and screw 20a.

In embodiments using a compression screw, first fastener 20a is inserted into the most distal end of first fastener hole 22a. In such embodiments, second fastener 20b is inserted into the most distal end of second fastener hole 22b. For the third and fourth fasteners 20c, 20d, in one embodiment, there are three options 1) static locking, 2) dynamic locking and 3) originally static with the option to later make dynamic. In one embodiment, if static locking only is desired, third fastener 20c is inserted into third fastener hole 20c to prevent nail 18 from moving relative to tibia 16. In one embodiment, if dynamic locking only is desired, fourth fastener 20d is inserted into the most proximal end of fourth fastener hole 22d. In one embodiment, if it is desired to have nail 18 be static but keep the option to later make dynamic, fourth fastener 20d is inserted into the most proximal end of fourth fastener hole 22d and third fastener 20c is inserted into third fastener hole 20c. Such an embodiment prevents nail 18 from moving relative to tibia 18 until third fastener 20c is removed at which point nail 18 may move proximally up tibia 16 if calcaneus 12 and/or talus 14 are compressed further toward tibia 16 (e.g., if bone graft compresses).

Figure 21:
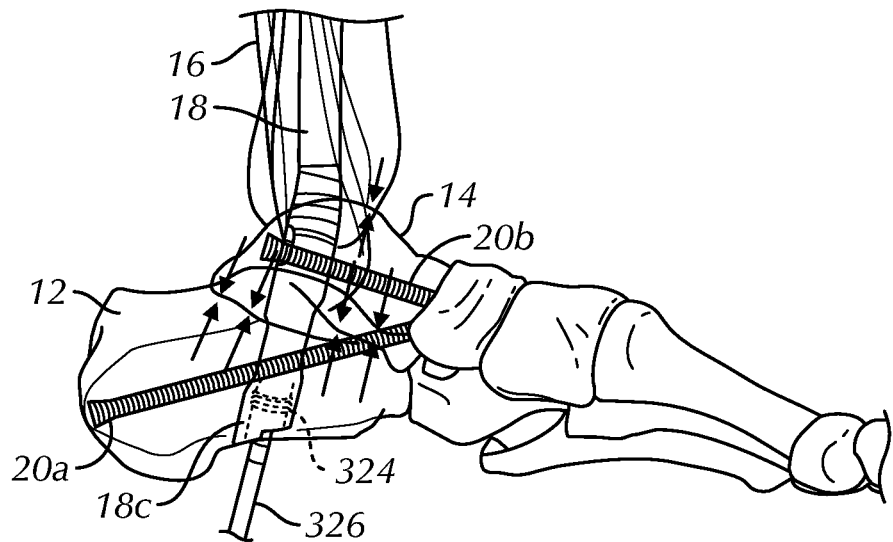
FIG. 21 is a medial elevational view of a compression system of the ankle fusion device of FIG. 1.

Referring to FIG. 21, once ankle fusion device 10 has been implanted, in embodiments having a compression configuration, compression screw 324 may be driven proximally through bore 18e using a screw driver 326. In one embodiment, as compression screw 324 is driven proximally, compression screw 324 engages first fastener 22a. Since calcaneus 12 is fixed relative to first fastener 22a and nail 18 is prevented from moving distal due third and/or fourth fasteners 22c, 22d, the calcaneus is shifted proximally toward tibia 16. In one embodiment, once calcaneus 12 engages talus 14, in embodiments with an elongated second fastener hole 22b, both calcaneus 12 and talus 14 are shifted proximally toward tibia 16.

Figure 22:
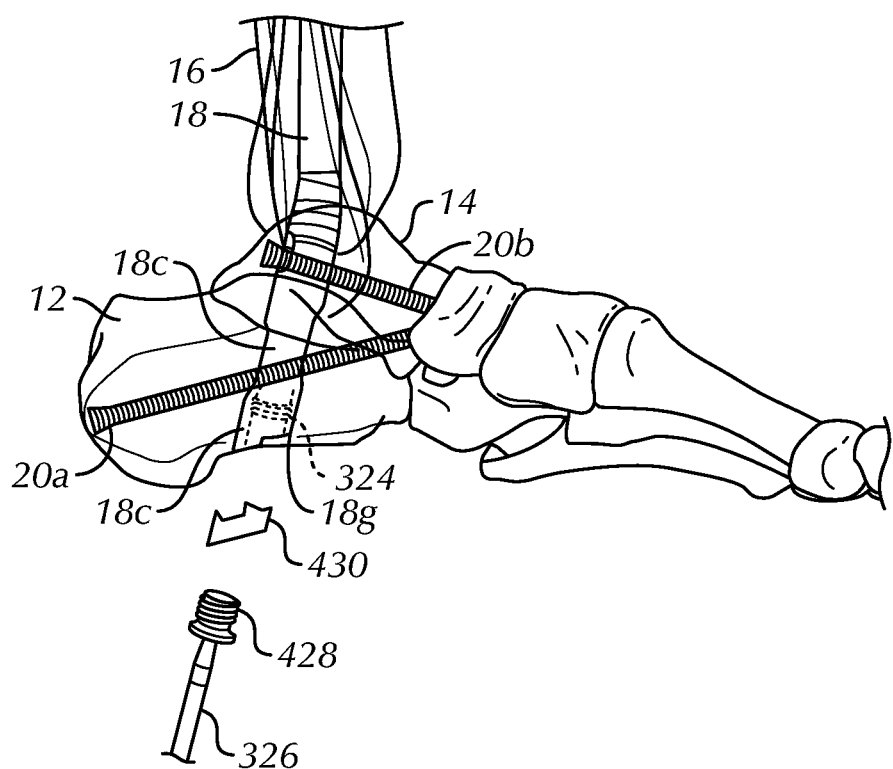
FIG. 22 is a medial elevational view of end cap sleeve and end cap screw of FIG. 4 being inserted in the ankle fusion device of FIG. 1A.
Figure 23A:
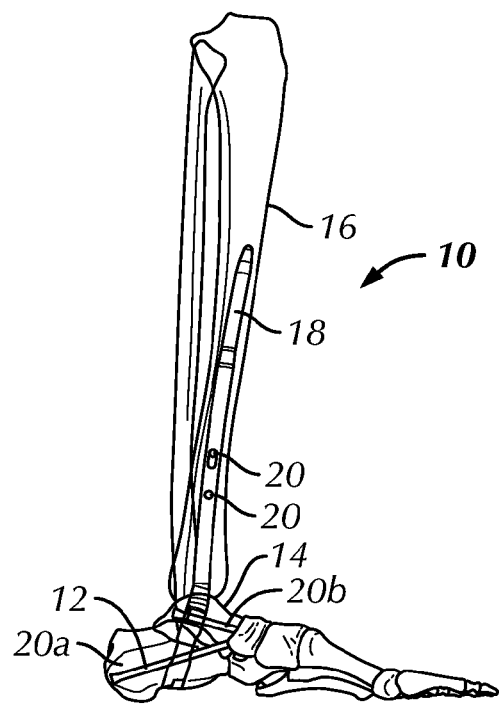
FIG. 23A is a medial elevational view of the implanted ankle fusion device of FIG. 1A.
Figure 23B:
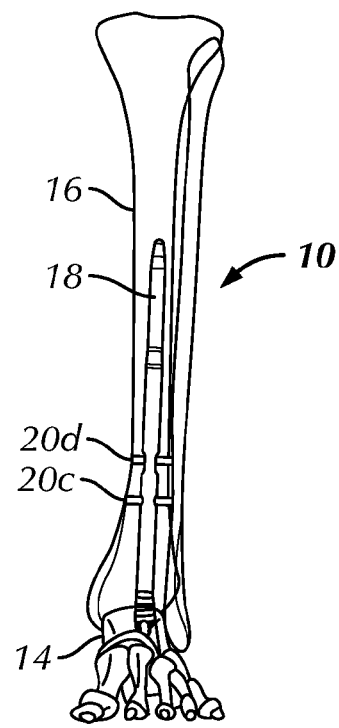
FIG. 23B is a lateral elevational view of the implanted ankle fusion device of FIG. 1A.
Figure 23C:
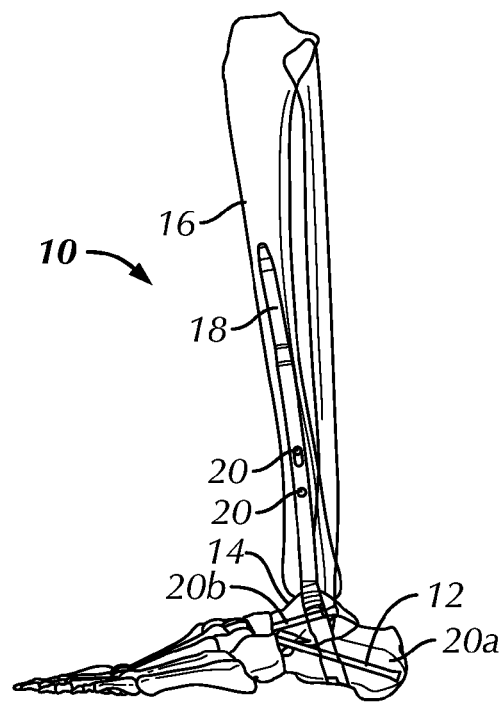
FIG. 23C is an anterior elevational view of the implanted ankle fusion device of FIG. 1A.
Figure 23D:
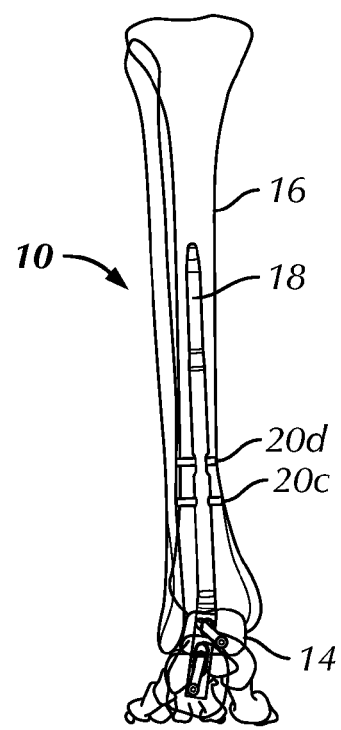
FIG. 23D is a posterior elevational view of the implanted ankle fusion device of FIG. 1A.

Referring to FIG. 22, once compression screw 324 is adjusted, in one embodiment, end cap sleeve 430 and end cap screw 428 may be inserted into distal end 18d of nail 18 to seal bore 183.

FIGS. 23A-23D illustrate an exemplary ankle fusion device 10 after installation. In one embodiment, ankle fusion device 10 is left implanted in the patient until calcaneus 12, talus 14 and/or tibia 16 are sufficiently fused together.

Figure 24:
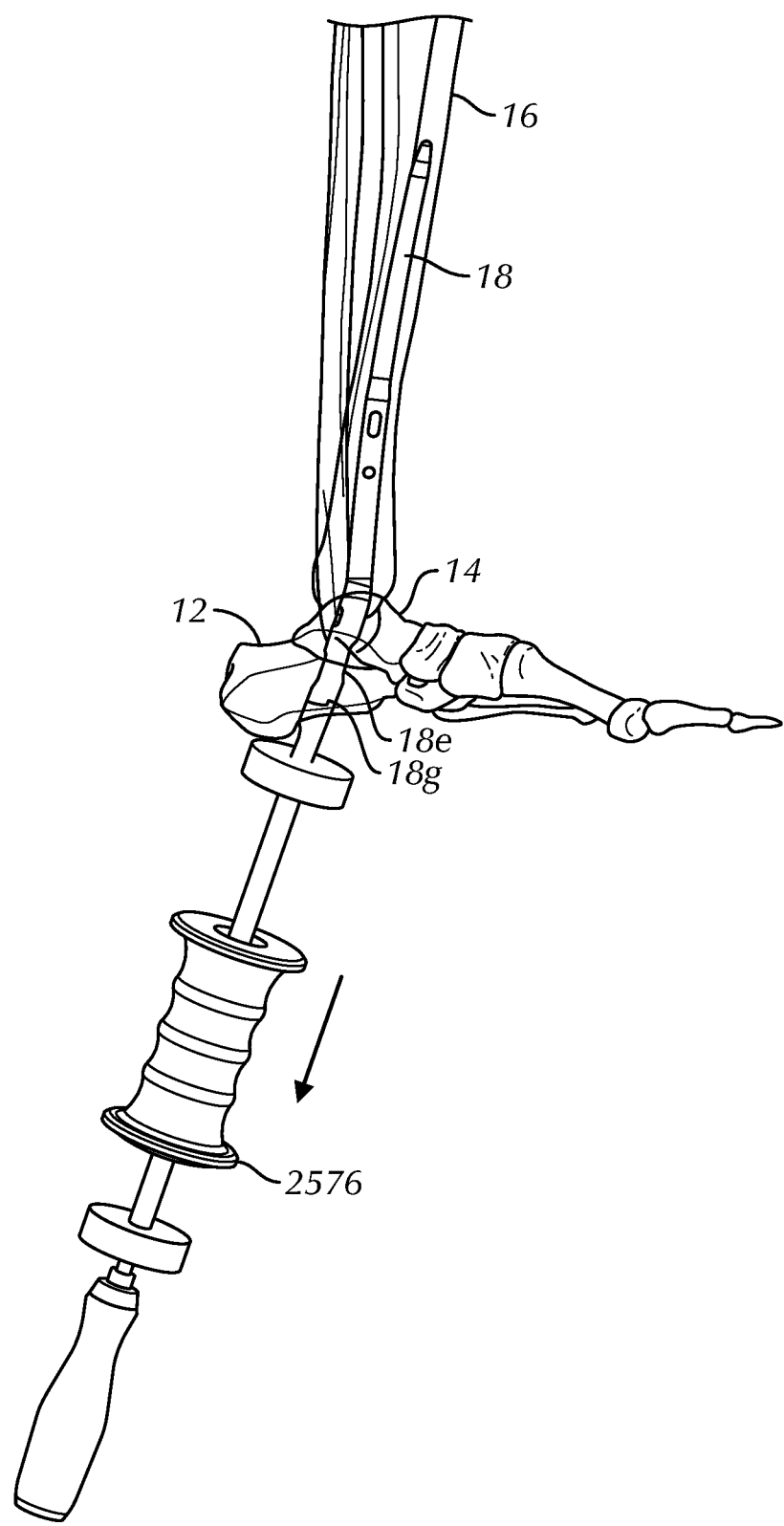
FIG. 24 is a medial elevational view of the implanted nail of FIG. 1A attached to an extraction tool in accordance with an exemplary embodiment of the present invention.

Referring to FIG. 24, in one embodiment, once fusion is complete or it is otherwise desired to remove ankle fusion device 10, an extraction tool 2576 may be used to assist in distracting nail 18 from the patient. In one embodiment, after removing fasteners 20 and end cap sleeve 430 and end cap screw 428, extraction tool 2576 is threadably attached to distal end 18d of nail 18. In one embodiment, extraction tool 2576 is pulled and/or hammered distally to remove nail 18.

In one embodiment, there is a kit for performing the ankle arthrodeses described herein. Such a kit may include one or more of each of the instruments, fasteners and/or implantable devices described herein. In one embodiment, a kit for performing ankle arthrodesis includes nail 18, one or more fasteners 20, guidewire targeting device 534, and at least one guidewire 1060. In one embodiment, a kit for performing ankle arthrodesis includes nail 18, one or more fasteners 20, guidewire targeting device 534, first guidewire 1060 and second guidewire 1062. In one embodiment, a kit for performing ankle arthrodesis includes guidewire targeting device 534, and at least one guidewire 1060. In one embodiment, a kit for performing ankle arthrodesis includes guidewire targeting device 534, at least one guidewire 1060, and aiming arm 1870.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

We claim:

1. An ankle fusion device comprising:
a proximal portion generally extending along a first longitudinal axis, the proximal portion including a proximal end and a first fastener hole, the proximal portion having an arcuate curve such that the proximal end is spaced a distance from the first longitudinal axis in a first direction, the first fastener hole configured to receive a first fastener along a first fastener axis; and
a distal portion extending to a distal end from the proximal portion along a second longitudinal axis, the second longitudinal axis being angled in second and third directions relative to the first longitudinal axis, the second direction being perpendicular to the first direction and the third direction being opposite the first direction, the distal portion including a second fastener hole configured to receive a second fastener along a second fastener axis.

2. The ankle fusion device of claim 1, wherein the second fastener hole is elongate and the distal portion further includes:
a bore extending proximally from the distal end along the second longitudinal axis, the bore being at least partially threaded; and
an elongate third fastener hole configured to receive a third fastener along a third fastener axis.

3. The ankle fusion device of claim 2, further comprising a compression screw configured to be received in the bore and translate therein along the second longitudinal axis.

4. The ankle fusion device of claim 3, wherein the compression screw includes an engagement portion having a concave surface configured to contact the third fastener when the third fastener is received in the third fastener hole, and a threaded portion attachable to the engagement portion and having external threads configured to engage the threads of the bore.

5. The ankle fusion device of claim 2, wherein the bore does not extend through the entire distal portion.

6. The ankle fusion device of claim 2 further comprising:
an end cap set screw having a closed distal end and external screws configured to engage the threads of the bore.

7. The ankle fusion device of claim 1, wherein the distal portion includes a third fastener hole configured to receive a third fastener along a third fastener axis.

8. The ankle fusion device of claim 7, wherein the second fastener axis is oriented at an oblique angle relative to the third fastener axis.

9. The ankle fusion device of claim 7, wherein the third fastener axis is configured to be substantially aligned with a longest dimension of a talus once the ankle fusion device is implanted.

10. The ankle fusion device of claim 1, wherein the proximal portion further comprises a fourth fastener hole configured to receive a fourth fastener along a fourth fastener axis.

11. The ankle fusion device of claim 10, wherein the fourth fastener axis and the first fastener axis are substantially parallel.

12. The ankle fusion device of claim 10, wherein the fourth fastener hole is elongate.

13. The ankle fusion device of claim 1, wherein the distal end includes a truncated surface that is generally perpendicular to the first longitudinal axis and oriented at an oblique angle relative to the second longitudinal axis.

14. The ankle fusion device of claim 1, wherein the second fastener axis is configured to be substantially aligned with a longest dimension of a calcaneus bone once the ankle fusion device is implanted.

15. The ankle fusion device of claim 1, wherein the ankle fusion device is configured and dimensioned such that once the ankle fusion device is implanted in a body the proximal portion extends into a tibia, the distal portion extends through a calcaneus, the first direction is in an anterior direction, the second direction is in a lateral direction and the third direction is in a posterior direction.

16. The ankle fusion device of claim 1, wherein the entire proximal portion is arcuate in the first direction.

17. The ankle fusion device of claim 1, wherein the proximal portion is least partially cannulated.

18. The ankle fusion device of claim 1, wherein the proximal portion is substantially solid.

19. The ankle fusion device of claim 1, wherein the first fastener axis is perpendicular to the first direction.

* * * * *